US008440671B2

(12) United States Patent
Held

(10) Patent No.: US 8,440,671 B2
(45) Date of Patent: May 14, 2013

(54) COMPOSITIONS COMPRISING A PHOSHODIESTERASE-5 INHIBITOR AND THEIR USE IN METHODS OF TREATMENT

(75) Inventor: Jerry M. Held, Santa Fe, NM (US)

(73) Assignee: Vivus, Inc., Mountain View, CA (US)

( * ) Notice: Subject to any disclaimer, the term of this patent is extended or adjusted under 35 U.S.C. 154(b) by 0 days.

(21) Appl. No.: 12/600,637

(22) PCT Filed: May 19, 2008

(86) PCT No.: PCT/US2008/006467
§ 371 (c)(1),
(2), (4) Date: Oct. 28, 2010

(87) PCT Pub. No.: WO2008/144061
PCT Pub. Date: Nov. 27, 2008

(65) Prior Publication Data
US 2011/0034471 A1 Feb. 10, 2011

Related U.S. Application Data

(60) Provisional application No. 60/930,673, filed on May 18, 2007, provisional application No. 60/962,094, filed on Jul. 27, 2007.

(51) Int. Cl.
| | |
|---|---|
| A61K 31/15 | (2006.01) |
| A61K 31/50 | (2006.01) |
| A61K 31/495 | (2006.01) |
| A61K 31/135 | (2006.01) |
| A61K 31/497 | (2006.01) |
| A61K 31/53 | (2006.01) |
| A01N 33/24 | (2006.01) |
| A01N 43/58 | (2006.01) |
| A01N 43/60 | (2006.01) |
| A01N 33/02 | (2006.01) |
| A01N 43/90 | (2006.01) |
| A01N 43/64 | (2006.01) |
| A61K 31/519 | (2006.01) |

(52) U.S. Cl.
USPC ............... 514/250; 514/252.12; 514/253.02; 514/262.1; 514/243; 514/261.1; 514/640; 514/646

(58) Field of Classification Search .............. 514/243, 514/250, 252.12, 253.02, 261.1, 262.1, 640, 514/646

See application file for complete search history.

(56) References Cited

U.S. PATENT DOCUMENTS

| | | | |
|---|---|---|---|
| 5,962,463 | A | 10/1999 | Nitsch et al. |
| 2004/0067957 | A1 | 4/2004 | Jerussi et al. |
| 2005/0009835 | A1 | 1/2005 | Thomas |
| 2006/0235005 | A1 | 10/2006 | Goff |
| 2008/0081806 | A1 | 4/2008 | Held |
| 2008/0188480 | A1 | 8/2008 | Black et al. |
| 2009/0062313 | A1 | 3/2009 | Kass et al. |

FOREIGN PATENT DOCUMENTS

| | | |
|---|---|---|
| FR | 2810886 A1 | 1/2002 |
| WO | 01/78711 A2 | 10/2001 |
| WO | 02/089808 A1 | 11/2002 |
| WO | 03/028730 A2 | 4/2003 |
| WO | 03/056899 A2 | 7/2003 |
| WO | WO 2005/089766 A1 * | 9/2005 |
| WO | WO 2006/001877 A2 * | 1/2006 |
| WO | 2006/016262 A1 | 2/2006 |
| WO | 2006/091542 A2 | 8/2006 |

OTHER PUBLICATIONS

Burke et al. (2006), "Clinical Neurosciences 2005 Meeting, Torquay, England, Sep. 7-9, 2005 / Effect of Sildenafil citrate (Viagra) on cerebral blood flow in patients with multiple sclerosis", J of Neurology Neurosurgery & Psychiatry, 77(1):130.
Salonia et al. (2002), "A Prospective Study Comparing Paroxetine Alone Versus Paroxetine Plus Sildenafil in Patients with premature ejaculation", J of Urology, 168(6):2486-2489.
Swope (2000), "Preliminary Report: Use of Sildenafil to Treat Dyskinesias in Patients with Parkinson's Disease", Neurology, 54(7):A90.
Uthayathas et al. (2007), "Versatile effects of sildenafil: recent pharmacological applications", Pharmacological Reports, 59(2):150-163.
International Search Report, Application No. PCT/US2008/006467, Date: Dec. 29, 2008.
International Preliminary Report on Patentability, Application No. PCT/US2008/006467, Date: Nov. 24, 2009.
Misery (1997), "Skin, immunity and the nervous system", British Journal of Dermatology, 137(6):845-850.
Chateau (2007), "In Vitro Reconstruction of Neuro-Epidermal Connections", Investigative Dermatology, 127:4.
Sancero (2006), "Role of Neuropeptides in Psoriasis", British Journal of Dermatology, 155(5):876-882.
Kassis et al. (1977), "Synthesis of Prostaglandins in Psoriatic Skin", Archives of Dermatological Research, 259:207-212.
Caley et al. 'Extrapyramidal reactions and the selective serotonin-reuptake inhibitors', Ann Pharmacother, 31(12):1-9 (1997).
Gibbons et al. 'Microglia induce neural cell death via a proximity-dependent mechanism involving nitric oxide', Brain Res., 1084(1):1-15 (2006).
Hoffpauir et al. 'Nitric oxide transiently converts synaptic inhibition to excitation in retinal amacrine cells', J. Neurophysiol., 95(5):2866-77 (2006).

(Continued)

Primary Examiner — Kara R McMillian
(74) Attorney, Agent, or Firm — Lathrop & Gage LLP; Sean M. Coughlin, Esq.

(57) ABSTRACT

The invention relates generally to novel pharmaceutical methods for the treatment of various conditions. Compositions comprising: at least one phosphodiesterase-5-inhibitor in combination with one or more of the following medications: a selective serotonin reuptake inhibitor; a serotonin-norepinephrine reuptake inhibitor; a cholinesterase inhibitor; a dopamine agonist; or a medication suitable to increase the chemical concentrations of the neurotransmitters, selected from amino acids, monoamines, neuropeptides and other agents capable of primary neurotransmission in the synaptic clefts, and their use for treating a neurodegenerative disease in a subject. The invention also relates to: Compositions comprising: at least one phosphodietersa-5-inhibitor in combination with one or more of the following medications: a selective serotonin reuptake inhibitor; or a cholinesterase inhibitor, and their use for treating damaged skin in a subject.

9 Claims, 1 Drawing Sheet

OTHER PUBLICATIONS

Petracca et al. "A Double-Blind, Placebo—Controlled Study of Fluoxetine with Depressed Patients With Alzheimer's Disease", International Psychogeriatrics, 13(2): 233-40 (2001).

Munro et al. "Cognitive Response to Pharmacological Treatment for Depression in Alzheimer Disease", Am. J. Geriatr. Psychiatry 12(5): 491-98 (2004).

Lysketsos et al. "Treating Depression in Alzheimer Disease", Arch. Gen. Psychiatry 60:737-746 (2003).

Patel, "Pharmacotherapy of Cognitive Impairment in Alheinmer's Disease: A Review", Journal of Geriatric Psychiatry and Neurology, 8:81-95 (1995).

* cited by examiner

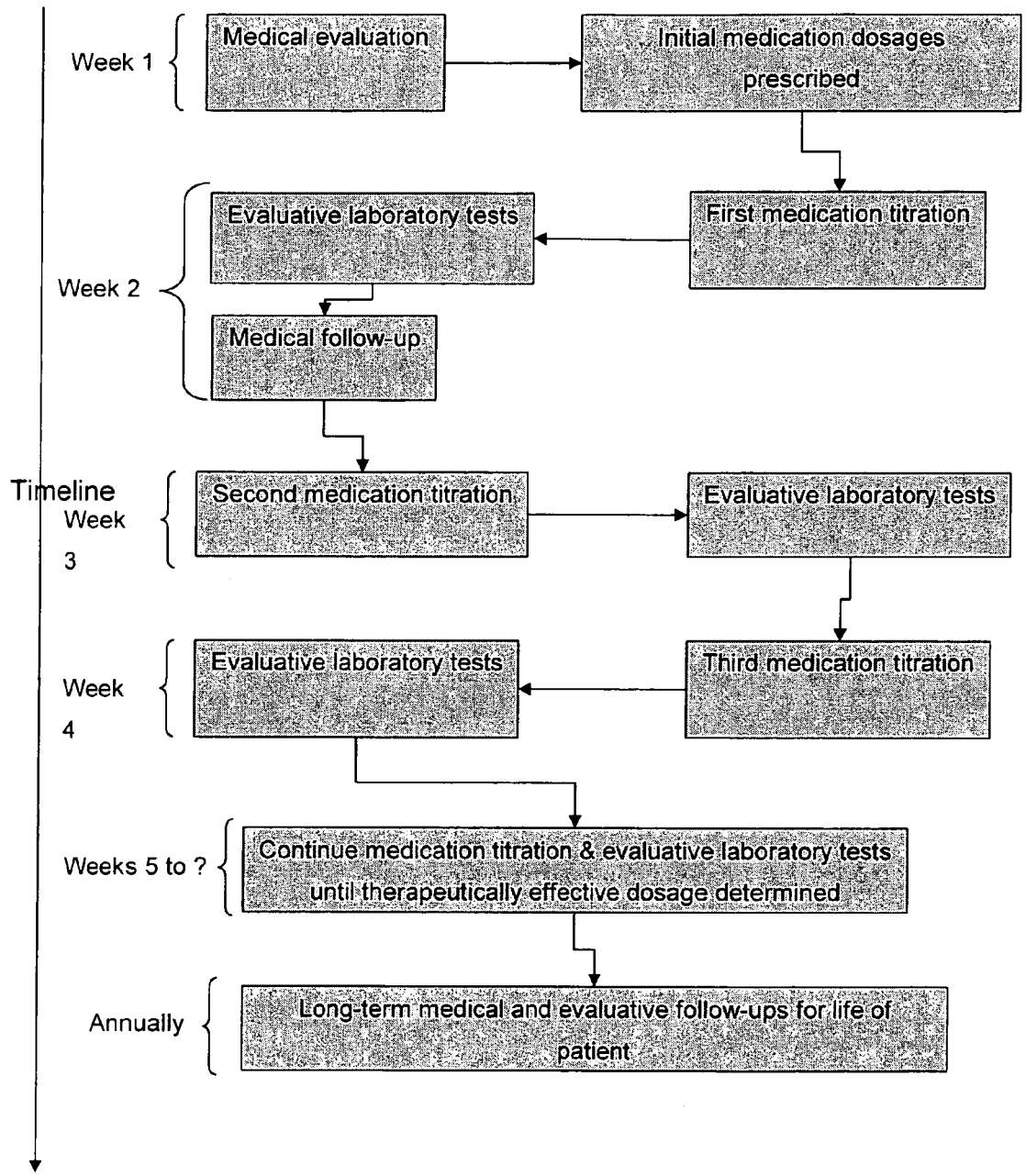

COMPOSITIONS COMPRISING A PHOSHODIESTERASE-5 INHIBITOR AND THEIR USE IN METHODS OF TREATMENT

CROSS-REFERENCE TO RELATED APPLICATIONS

This application claims priority to provisional U.S. Patent Application Ser. No. 60/930,673, filed May 18, 2007 and U.S. Patent Application Ser. No. 60/962,094, filed Jul. 27, 2007, each of which is incorporated herein by reference in its entirety. This application is a 35 U.S.C. §371 National Phase Application of PCT/US2008/006467, filed May 19, 2008 of which the contents are hereby fully incorporated by reference.

TECHNICAL FIELD

The invention relates generally to novel pharmaceutical compositions and methods for the treatment of various conditions, disorders, and diseases, and more particularly relates to the treatment of such conditions, disorders, and diseases using therapeutic agents that include a phosphodiesterase-5 inhibitor (PI-5) in combination with one or more agents. In certain aspects, the PI-5 is administered in combination with at least one or more Selective Serotonin Reuptake Inhibitors (SSRIs), Serotonin-norepinephrine Reuptake Inhibitors (SN-RIs), Cholinesterase Inhibitors (CIs), Dopamine Agonists (DIs) or any suitable agents that increase the chemical concentrations of other neurotransmitters, such as amino acids, monoamines, neuropeptides and other agents capable of primary neurotransmission in the synaptic clefts (OIs).

BACKGROUND OF THE INVENTION

The nervous system consists of the Central Nervous System (CNS) which consists of the brain and spinal cord and serves as the collection point of nerve impulses and the Peripheral Nervous System (PNS) which includes all of the nerves other than the brain or spinal cord and connects all parts of the body to the central nervous system. The peripheral (sensory) nervous system first receives stimuli and then the central nervous system interprets them with the peripheral (motor) nervous system initiating responses.

Neurotransmitters are chemicals that allow the movement of information from one neuron across the gap between it and the adjacent neuron. The release of neurotransmitters from one area of a neuron and the recognition of the chemicals by a receptor site on the adjacent neuron causes an electrical reaction that facilitates the release of the neurotransmitter and its movement across the gap. As such, neurotransmitters are essential for interneuronal signaling, and the specification of appropriate transmitters in differentiating neurons has been related to intrinsic neuronal identity and to extrinsic signaling proteins. Accordingly, many illnesses and disorders result from or relate to the over- or under-production of neurotransmitters.

Acetylcholine is one example of a neurotransmitter which is particularly important in the stimulation of muscle tissue. After stimulation, acetylcholine degrades to acetate and choline, which are absorbed back into the first neuron to form another acetylcholine molecule. The poison curare blocks transmission of acetylcholine. Some nerve gases inhibit the breakdown of acetylcholine, producing a continuous stimulation of the receptor cells, and spasms of muscles such as the heart. Epinephrine (adrenaline) and norepinephrine are neurotransmitters that are secreted principally from the adrenal gland. Secretion causes an increased heart rate and the enhanced production of glucose as a ready energy source (the "fight or flight" response). In addition, another neurotransmitter, Dopamine facilitates critical brain functions and, when unusual quantities are present, abnormal dopamine neurotransmission may play a role in Parkinson's disease, certain addictions, and schizophrenia. Serotonin is another exemplary neurotransmitter which is synthesized from the amino acid tryptophan and is assumed to play a biochemical role in mood and mood disorders, including anxiety, depression, and bipolar disorder.

Neurodegenerative diseases are chronic degenerative diseases of the central nervous system that may often lead to dementia. Although the causes and mechanisms of this collection of brain diseases are not well known, they are increasing in incidence in the developed as well as the underdeveloped world and are often found in the aging population. These diseases are characterized by molecular changes in nerve cells that result in nerve cell degeneration and ultimately nerve dysfunction and cell death. Examples of neurodegenerative disease include Alzheimer's disease, Parkinson's disease, multiple sclerosis, amyotrophic lateral sclerosis, frontotemporal dementia with Parkinson's features, progressive supranuclear palsies, essential dyskinesias, and dementia, to name a few, but there are additionally a wide variety of less common but related conditions.

Although much progress toward understanding neurodegenerative diseases has been made in recent years, few effective treatments and no cures are currently available.

In addition, the neuroimmunocutaneous system (NS) is composed of the nervous system, endocrine system, and immune system wherein each component is not distinct but rather function together as a single, integrated unit. Normal human skin expresses a variety of neuropeptides, including neuromediators and neurohormones, that are either directly derived from sensory neurons or from skin cells such as keratinocytes. Neuropeptides can be antidromically released from peripheral nerves into the skin and are implicated in the so-called neurogenic inflammation. They also exert various functions within the immune system and are thought to act as trophic substances as well as cytokines.

As such, the central and peripheral nervous system plays an influential role in the functioning of the NS. It is noted, for example, that over 80% of epidermal Langerhans cells have connections with axons of the cutaneous nerves. Autonomic connections to the enteric tract are likewise extensive. Neurons secrete a multitude of neuromediators, including vasoactive intestinal peptide, somatostatin, calcitonin gene-related peptide, substance p, neurotensin, catecholamines, endorphins and cyclic nucleotides. In addition, receptors are commonly found on cell surface membranes for serotonin, acetylcholine and other neurotransmitters. Various of these neuromediators have been shown to modulate inflammation and other properties and activities in the human skin and mucous membranes (British Journal of Dermatology, 137(6), 845-850, December 1997/L. Misery; Journal of Investigative Dermatology, 127: April 2007, Yannick Chateau, "In Vitro Reconstruction of Neuro-Epidermal Connections;" British Journal of Dermatology, 155(5), 876-882, 2006/Sancero, "Role of Neuropeptides in Psoriasis;" Archives of Dermatological Research, 259:3/January 2007/Frosch, N., "Synthesis of Prostaglandins in Psoriatic Skin.")

Skin conditions or dermatological disorders afflict millions of people each day. These skin conditions may be acute (lasting for just a few minutes to a few hours) or chronic conditions that may plague an individual for days, months, years or even a lifetime. A multitude of different dermatological conditions exist and may be fungal, bacterial, or viral based, or may be a non-infective, immunological response such as an inflammatory response with or without an allergic component, or may be idiopathic. Accordingly, symptoms may vary and may range from mild itching, redness and swelling to severe pustules and open sores and even in certain instances may lead to debilitating manifestations such as disabling ulcerations. Regardless of the cause or particular symptoms, dermatological disorders may substantially affect the quality of an individual's life. Examples of various diseases include atopy, psoriasis, contact dermatitis, acne, cancer, vasculitis and as well as traumatic processes such as surgery, laceration, burns, and infections, each of which can adversely impact the body and its appearance.

Despite the known and demonstrable connections and interrelationships between the human nervous and mucocutaneous, systems, little progress has been made in the treatment of wounds, scars and other diseases, disorders and traumas of the skin and mucous membranes. In general, typical treatment still relies primarily upon archaic techniques of limited utility and efficacy such as debridment, suturing and oral and topical antibiotics.

Accordingly, a new methodology is needed in the treatment of diseases, disorders and traumas of the skin and mucous membranes utilizing and exploiting the interrelationship between the nervous and muco-cutaneous systems.

While society has seen tremendous advances in the field of pharmaceuticals, there are, of course, drawbacks to the administration of any given pharmaceutical agent. Sometimes, the disadvantages, characterized as "side effects," are so severe as to preclude administration of a particular agent at a therapeutically effective dose. In such a case, drug therapy is discontinued, and other pharmaceutical agents may be tried. Many agents in the same therapeutic class, however, display similar side effect profiles, meaning that patients either have to forego therapy or suffer from unpleasant side effects associated with a particular medication.

The pervasiveness of neurodegenerative diseases, skin wounds, scars and other diseases, disorders and traumas of the skin and mucous membranes, and their devastating impact on a patient, his/her family and society in general as well as the dearth of effective and affordable treatments compel a new and innovative approach to their treatment and remission. Accordingly, there is interest in the development of novel methods and compositions for treating such diseases and conditions. In addition, combination treatment may be employed to decrease the doses of the individual components in the resulting combinations while still preventing unwanted or harmful side effects of the individual components. Thus, there is a need to discover suitable methods for the treatment of neurodegenerative diseases, skin wounds, scars and other diseases, disorders and traumas of the skin and mucous membranes, including combination treatments and dosing strategies that result in reduction of toxicity, decreased side effects and increased therapeutic effectiveness.

SUMMARY OF THE INVENTION

The invention is directed to novel pharmaceutical compositions and methods for the treatment of various conditions, disorders, and diseases, and more particularly relates to the treatment of such conditions, disorders, and diseases using therapeutic agents that include a phosphodiesterase-5 inhibitor (PI-5) in combination with one or more agents.

In certain aspects, the present invention also features a pharmaceutical composition that includes a phosphodiesterase-5 inhibitor in combination with one or more additional agents, e.g., Selective Serotonin Reuptake Inhibitors (SSRIs), Serotonin-norepinephrine Reuptake Inhibitors (SNRIs), Cholinesterase Inhibitors (CIs), Dopamine Agonists (DIs) or any suitable medications to increase the chemical concentrations of other neurotransmitters, such as amino acids, monoamines, neuropeptides and other agents capable of primary neurotransmission in the synaptic clefts (OIs).

In certain aspects, the pharmaceutical composition may include one or more PI-5s in combination with one or more additional agents, e.g., Selective Serotonin Reuptake Inhibitors (SSRIs), Serotonin-norepinephrine Reuptake Inhibitors (SNRIs), Cholinesterase Inhibitors (CIs), Dopamine Agonists (DIs) or any suitable medications to increase the chemical concentrations of other neurotransmitters, such as amino acids, monoamines, neuropeptides and other agents capable of primary neurotransmission in the synaptic clefts (OIs).

In certain aspects, the present invention is directed to a novel composition for treating a neurodegenerative disease in a subject includes a phosphodiesterase-5 inhibitor (PI-5) in combination with one or more Selective Serotonin Reuptake Inhibitors (SSRIs), Serotonin-norepinephrine Reuptake Inhibitors (SNRIs), Cholinesterase Inhibitors (CIs), Dopamine Agonists (DI) or any suitable medications to increase the chemical concentrations of other neurotransmitters, such as amino acids, monoamines, neuropeptides and other agents capable of primary neurotransmission in the synaptic clefts (OIs).

In certain aspects, the composition for treating a neurodegenerative disease includes a PI-5 selected from CIALIS® (tadalafil), LEVITRA® (vardenafil) and VIAGRA® (sildenafil).

In certain aspects, the composition for treating a neurodegenerative disease includes a SSRI selected from LUVOX® (fluvoxamine), PROZAC® (fluoxetine), CELEXA® (citalopram), ZOLOFT® (sertraline) and PAXIL® (paroxetine).

In certain aspects, the composition for treating a neurodegenerative disease includes a SNRI selected from EFFEXOR® (venlafaxine) and CYMBALTA® (duloxetine).

In certain aspects, the composition for treating a neurodegenerative disease includes a CI medication selected from COGNEX® (tacrine) and ARICEPT® (donepezil).

In certain aspects, the composition for treating a neurodegenerative disease includes a DI selected from bromocryptine, SINEMET® (carbidopa-levodopa) and MIRAPEX® (pramipexole).

In certain aspects, the composition for treating a neurodegenerative disease includes any suitable medication to increase the chemical concentrations of other neurotransmitters, such as amino acids, monoamines, neuropeptides and other agents capable of primary neurotransmission in the synaptic clefts (OIs).

In certain aspects of the present invention, the OIs may be epinephrine, norepinephrine, dopamine, serotonin, melatonin, glutamic acid, gamma aminobutyric acid, aspartic acid, glycine, adenosine, ATP, GTP, vasopressin, somatostatin, neurotensin, leuteinizing hormone, insulin, histamine, nitrogen monoxide, carbon monoxide, acetylcholine, octopamine, tyramine, gastrin, cholecystokinin, oxytocin, neurophysin I, neurophysin II, neuropeptide Y, pancreatic polypeptide, peptide YY, corticotrophin, dynorphin, endorphin, enkephaline, secretin, motilin, glucagons, vasoactive intestinal peptide, growth hormone releasing factor, neurokinin A, neurokinin B, substance P, bombesin, gastrin releasing peptide or anandamide.

In certain aspects, the combination medications for treating a neurodegenerative disease are administered individually.

In certain aspects, the combination medications for treating a neurodegenerative disease are in a combined form such as a once-weekly patch, a monthly patch, a long-term injection, a combined pill, or an implant.

In certain embodiments, the invention is directed to a method for treating a neurodegenerative disease in a subject comprising administering to the subject a composition which includes a PI-5 in combination with at least one or more Selective Serotonin Reuptake Inhibitors (SSRIs), Serotonin-norepinephrine Reuptake Inhibitors (SNRIs), Cholinesterase Inhibitors (CIs), Dopamine Agonists (DIs) or any suitable agents that increase the chemical concentrations of other neurotransmitters, such as amino acids, monoamines, neuropeptides and other agents capable of primary neurotransmission in the synaptic clefts (OIs).

In certain aspects, the method for treating a neurodegenerative disease includes administering the medications separately.

In certain aspects, the method for treating a neurodegenerative disease includes administering the medications in a combined form.

In certain aspects of the invention, the neurodegenerative disease is Alzheimer's disease, Parkinson's disease, multiple sclerosis, amyotrophic lateral sclerosis, fronto-temporal dementia with Parkinson's features, progressive supranuclear palsies, essential dyskinesias, or dementia.

In certain aspects of the invention, the neurodegenerative disease is Alzheimer's disease.

In certain aspects of the invention, the neurodegenerative disease is Parkinson's disease.

In certain aspects of the invention, the neurodegenerative disease is multiple sclerosis.

In certain aspects of the invention, the neurodegenerative disease is amyotrophic lateral sclerosis.

In certain aspects of the invention, the neurodegenerative disease is fronto-temporal dementia with Parkinson's features.

In certain aspects of the invention, the neurodegenerative disease is progressive supranuclear palsies, essential dyskinesias, or dementia.

In certain aspects of the invention, the neurodegenerative disease is an essential dyskinesia or dementia.

In certain aspects of the invention, the neurodegenerative disease is dementia.

In certain embodiments, the invention is directed to the use of a PI-5 in the manufacture of a medicament for treating a neurodegenerative disease, wherein the composition further includes at least one or more Selective Serotonin Reuptake Inhibitors (SSRIs), Serotonin-norepinephrine Reuptake Inhibitors (SNRIs), Cholinesterase Inhibitors (CIs), Dopamine Agonists (DIs) or any suitable agents that increase the chemical concentrations of other neurotransmitters, such as amino acids, monoamines, neuropeptides and other agents capable of primary neurotransmission in the synaptic clefts (OIs).

In certain embodiments, the invention is directed towards a kit comprising a packaged combination of a PI-5 with one or more SSRIs, SNRIs, CIs, DIs or any suitable medication to increase the chemical concentrations of other neurotransmitters, such as amino acids, monoamines, neuropeptides and other agents capable of primary neurotransmission in the synaptic clefts (OIs) in separate and discrete dosage forms, and instructions for its use.

In certain embodiments, the invention is directed towards a method for treating a neuro-degenerative dementia (NDD) in a subject comprising administering to the subject a composition comprising a phosphodiesterase-5 inhibitor (PI-5) in combination with one or more of Selective Serotonin Reuptake Inhibitors (SSRIs) or Cholinesterase Inhibitors (CIs).

In certain aspects of this embodiment, the combination includes a PI-5, SSRI, and a CI, e.g., CIALIS® (tadalafil), LUVOX® (fluvoxamine) and COGNEX® (tacrine).

In certain aspects of this embodiment, the CIALIS® (tadalafil) is administered at a dosage ranging from 20 mg to 100 mg/day.

In certain aspects of this embodiment, the LUVOX® (fluvoxamine) is administered at a dosage ranging from 25 mg to 400 mg/day.

In certain aspects of this embodiment, the COGNEX® (tacrine) is administered at a dosage ranging from 10 mg to 160 mg/day.

In certain embodiments, the invention is directed towards the use of a phosphodiesterase-5 inhibitor (PI-5) in the manufacture of a medicament for treating neuro-degenerative dementia (NDD) in a subject, wherein the composition includes one or more of the following: Selective Serotonin Reuptake Inhibitors (SSRIs) or Cholinesterase Inhibitors (CIs).

In certain embodiments, the present invention is directed to novel compositions and methods for improving the appearance and health of normal skin and mucous membranes, and/or for facilitating and accelerating the healing of damaged skin and mucous membranes.

In certain embodiments, the present invention is directed to a novel composition for treating damaged skin in a subject that includes a phosphodiesterase-5 inhibitor (PI-5) in combination with one or more. Selective Serotonin Reuptake Inhibitors (SSRIs) or Cholinesterase Inhibitors (CIs).

In certain aspects, the novel composition for treating skin damage includes a PI-5 which is selected from CIALIS® (tadalafil), LEVITRA® (vardenafil) and VIAGRA® (sildenafil).

In certain aspects, the novel composition for treating skin damage includes at least one or more SSRIs selected from LUVOX® (fluvoxamine), PROZAC® (fluoxetine), CELEXA® (citalopram), ZOLOFT® (sertraline) and PAXIL® (paroxetine).

In certain aspects, the novel composition for treating skin damage includes at least one or more CIs selected from COGNEX® (tacrine) and ARICEPT® (donepezil).

In certain aspects, the medications for treating skin damage are administered individually.

In certain aspects, the medications for treating skin damage are in a combined form such as a once-weekly or monthly patch, a long-term injection, a combined pill, or an implant.

In certain aspects, the invention is directed to a method for treating skin damage in a subject comprising administering to the subject a composition which includes a PI-5 in combination with at least one or more Selective Serotonin Reuptake Inhibitors (SSRIs) or Cholinesterase Inhibitors (CIs).

In certain aspects, the method for treating skin damage includes administering the medications separately.

In certain aspects of the invention, the skin damage is atopy, psoriasis, contact dermatitis, acne, cancer, or vasculitis.

In certain aspects of the invention, the skin damage is psoriasis.

In certain aspects of the invention, the skin damage is contact dermatitis.

In certain aspects of the invention, the skin damage is acne.

In certain aspects of the invention, the skin damage is cancer.

In certain aspects of the invention, the skin damage is vasculitis.

In certain aspects of the invention, the skin damage is a result of a traumatic process.

In certain aspects of the invention, the traumatic process is surgery, a laceration, a burn or an infection.

In certain aspects of the invention, the traumatic process is surgery.

In certain aspects of the invention, the traumatic process is a laceration.

In certain aspects of the invention, the traumatic process is a burn.

In certain aspects of the invention, the traumatic process is an infection.

In certain embodiments, the invention is directed to the use of a PI-5 in the manufacture of a medicament for treating skin damage in a subject, wherein the composition further comprises at least one or more Selective Serotonin Reuptake Inhibitors (SSRIs).

In certain embodiments, the invention is directed towards a kit comprising a packaged combination of a PI-5 with one or more SSRIs or CIs in separate and discrete dosage forms, and instructions for its use.

In certain embodiments, the invention is directed towards a method for treating skin damage in a subject comprising administering to the subject a composition comprising a phosphodiesterase-5 inhibitor (PI-5) in combination with one or more Selective Serotonin Reuptake Inhibitors (SSRIs) or Cholinesterase Inhibitors (CIs).

In certain aspects of this embodiment, the PI-5 is CIALIS® (tadalafil), the SSRI is LUVOX® (fluvoxamine) and the CI is COGNEX® (tacrine).

In certain aspects of this embodiment, the CIALIS® (tadalafil) is administered at a dosage ranging from 5 mg to 80 mg/day.

In certain aspects of this embodiment, the LUVOX® (fluvoxamine) is administered at a dosage ranging from 12.5 mg to 400 mg/day.

In certain aspects of this embodiment, the COGNEX® (tacrine) is administered at a dosage ranging from 5 mg to 60 mg/day.

In certain embodiments, the invention is directed towards the use of a phosphodiesterase-5 inhibitor (PI-5) in the manufacture of a medicament for treating skin damage wherein the composition comprises one or more Selective Serotonin Reuptake Inhibitors (SSRIs) or Cholinesterase Inhibitors (CIs).

Without wishing to be bound by theory, in certain aspects of this embodiment, the PI-5 is CIALIS® (tadalafil), the SSRI is LUVOX® (fluvoxamine) and the CI is COGNEX® (tacrine).

Without wishing to be bound by theory, in certain aspects, the invention is directed to the administration of a PI-5 inhibitor which acts to increase synaptic levels of nitric oxide, which then acts both directly and indirectly on soluble guanylate cyclase to increase the formation of cyclic GMP.

Without wishing to be bound by theory, in certain aspects, the invention is directed to the administration of a PI-5 inhibitor in combination with a CI, wherein the CI acts to increase the level of synaptic acetylcholine.

Without wishing to be bound by theory, in certain aspects, the invention is directed to the administration of a PI-5 inhibitor in combination with a SSRI, wherein the SSRI acts to increase the level of synaptic serotonin.

In another aspect, the invention involves administering a combination of a PI-5 inhibitor with one or more agents which directly or indirectly reduces the unwanted side effects resulting from administration of the first agent or the other additionally administered agents.

In another aspect, the presented invention is directed to a novel methodology and system of pharmaceutical combinations for the treatment of neurodegenerative diseases, by administering a phosphodiesterase-5 inhibitor (PI-5) in combination with one or more other medications to increase neurotransmitters in order to augment neurotransmission in the areas of the brain where the respective neurotransmitters function.

The present invention, in one embodiment, features a novel therapy for treating neurodegenerative diseases such as Alzheimer's disease, Parkinson's disease, multiple sclerosis, amyotrophic lateral sclerosis, fronto-temporal dementia with Parkinson's features, progressive supranuclear palsies, essential dyskinesias or dementia.

In another aspect, the presented invention is directed to a novel methodology and system of pharmaceutical combinations for the facilitation and acceleration of wound, burn and scar healing or for the maintenance and improvement of skin and mucous membrane health, by administering a phosphodiesterase-5 inhibitor (PI-5) in combination with one or more SSRIs or CIs.

The present invention, in one embodiment, features a novel therapy for treating atopy, psoriasis, contact dermatitis, acne, cancer, vasculitis or any traumatic processes which can adversely impact body appearance, such as surgery, a laceration, a scar, a burn, or an infection.

In certain aspects, the present invention features methods of treating a subject with a phosphodiesterase-5 inhibitor.

In certain aspects, the treatment regime includes regular monitoring of relevant physiological functions, including, for example, blood tests for liver function, kidneys, and electrolytes, and/or physical exams, including EKG and treadmill tests.

BRIEF DESCRIPTION OF THE DRAWINGS

FIG. 1 provides an exemplary time line flowchart for administering and monitoring the use of the treatment of the current invention.

DETAILED DESCRIPTION OF THE INVENTION

Before describing the present invention in detail, it is to be understood that unless otherwise indicated, this invention is not limited to particular formulations, active and inactive agents, modes of administration, or methods of treatment or use, as such may vary. It is also to be understood that the terminology used herein is for the purpose of describing particular embodiments only, and is not intended to be limiting. The scientific publications, patents or patent applications cited in the various sections of this document are herein incorporated-by-reference for all purposes.

Definitions and Nomenclature:

It must be noted that, as used in this specification and the appended claims, the singular forms "a," "an" and "the" include plural referents unless the context clearly dictates otherwise. Thus, for example, "an active agent" refers not only to a single active agent but also to a combination of two or more different active agents, "a dosage form" refers to a combination of dosage forms as well as to a single dosage form, and the like. Unless defined otherwise, all technical and scientific terms used herein have the meaning commonly understood by one of ordinary skill in the art to which the invention pertains. Although any methods and materials similar or equivalent to those described herein may be useful in the practice or testing of the present invention, preferred methods and materials are described below. Specific terminology of particular importance to the description of the present invention is defined below.

When referring to an active agent, applicants intend the term "active agent" to encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

The terms "treating" and "treatment" as used herein refer to reduction in severity and/or frequency of symptoms, elimination of symptoms and/or underlying cause, and improvement or remediation of damage. In certain aspects, the terms "treating" and "treatment" as used herein refer to the prevention of the occurrence of symptoms and/or their underlying cause. Thus, "treating" a patient as described herein encompasses treating a neurodegenerative disease such as Alzheimer's disease, Parkinson's disease, multiple sclerosis, amyotrophic lateral sclerosis, fronto-temporal dementia with Parkinson's features, progressive supranuclear palsies, essential dyskinesias or dementia. In other embodiments, "treating" a patient as described herein encompasses the facilitation and acceleration of wound, burn and scar healing or for the maintenance and improvement of skin and mucous membrane health, e.g., a skin disease or dermatological disorder or trauma of the skin or mucous membranes such as atopy, psoriasis, contact dermatitis, acne, cancer, vasculitis or any traumatic processes such as surgery, laceration, burns, infections or any disease or condition that causes skin damage.

By the terms "effective amount" and "therapeutically effective amount" of an agent, compound, drug, composition or combination of the invention which is nontoxic and effective for producing some desired therapeutic effect upon administration to a subject or patient (e.g., a human subject or patient).

The term "dosage form" denotes any form of a pharmaceutical composition that contains an amount of active agent sufficient to achieve a therapeutic effect with a single administration. When the formulation is a tablet or capsule, the dosage form is usually one such tablet or capsule. The frequency of administration that will provide the most effective results in an efficient manner without overdosing will vary with the characteristics of the particular active agent, including both its pharmacological characteristics and its physical characteristics, such as hydrophilicity.

The term "controlled release" refers to a drug-containing formulation or fraction thereof in which release of the drug is not immediate, i.e., with a "controlled release" formulation, administration does not result in immediate release of the drug into an absorption pool. The term is used interchangeably with "nonimmediate release" as defined in *Remington: The Science and Practice of Pharmacy, Nineteenth Ed.* (Easton, Pa.: Mack Publishing Company, 1995). In general, the term "controlled release" as used herein includes sustained release and delayed release formulations.

The term "sustained release" (synonymous with "extended release") is used in its conventional sense to refer to a drug formulation that provides for gradual release of a drug over an extended period of time, and that preferably, although not necessarily, results in substantially constant blood levels of a drug over an extended time period. The term "delayed release" is also used in its conventional sense, to refer to a drug formulation which, following administration to a patient, provides a measurable time delay before drug is released from the formulation into the patient's body.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree. The term "pharmaceutically acceptable salts" include acid addition salts which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Active Agent Combinations:

The present invention is directed to novel pharmaceutical compositions and methods for the treatment of various conditions, disorders, or diseases, and more particularly relates to the treatment of such conditions, disorders, or diseases using therapeutic agents that include a phosphodiesterase-5 inhibitor (PI-5) in combination with one or more agents. In certain aspects, the PI-5 is administered in combination with at least one or more Selective Serotonin Reuptake Inhibitors (SSRIs), Serotonin-norepinephrine Reuptake Inhibitors (SNRIs), Cholinesterase Inhibitors (CIs), Dopamine Agonists (DIs) or any suitable agent that increases the chemical concentrations of other neurotransmitters, such as amino acids, monoamines, neuropeptides and other agents capable of primary neurotransmission in the synaptic clefts (OIs).

The compositions of the present invention may be administered to a patient for the pharmaceutical treatment of neurodegenerative diseases. For instance, the invention provides for neurodegenerative diseases such as Alzheimer's disease, Parkinson's disease, multiple sclerosis, amyotrophic lateral sclerosis, fronto-temporal dementia with Parkinson's features, progressive supranuclear palsies, essential dyskinesias and dementia. The subject invention involves treating a subject with a PI-5 in combination with one or more SSRIs, SNRIs, CIs, DIs or OIs.

As such, the current invention is directed to a new method and composition for the treatment of neurodegenerative diseases by administering a combination of a PI-5 with one or more medications to increase target neurotransmitters including, without limitation, SSRIs, SNRIs, CIs, NIs, DIs or OIs. By combining the agents according to the present invention, each reduces the side effects of the other agent and both contribute to the pharmacology efficacy for treating neurodegenerative diseases. As such, the current invention is directed to a new method and composition for the treatment of neurodegenerative diseases by administering a combination of a PI-5 with one or more medications to increase target neurotransmitters including, without limitation, SSRIs, SNRIs, CIs, NIs, DIs or OIs.

Moreover, the compositions of the present invention may be administered to a patient to improve the appearance and health of normal skin and mucous membranes and to facilitate or accelerate the healing of damaged skin. For instance, the invention provides for treating various diseases (atopy, psoriasis, contact dermatitis, acne, cancer, vasculitis or traumatic processes such as a surgery, a laceration, a burn or an infection which adversely impact the body appearance. The subject invention involves treating a subject with a PI-5 in combination with one or more SSRIs or CIs.

As such, the current invention, is further directed to a new method and composition for facilitating or accelerating wound, burn and scar healing and for the maintenance and improvement of skin and mucous membrane health by administering a combination of a PI-5 with one or more agents, each of which modulate the activity of the peripheral and central nervous systems, particularly at the level of the transcutaneous nerves, which in turn result in the modulation of secretion and activity of the various neuropeptides and neurohormones by the transcutaneous and autonomic nerves including, without limitation, an SSRI or a CI.

Essentially, virtually all neurotransmission in both the central and peripheral nervous systems requires two chemical agents. The first agent is the traditional or primary neurotransmitter entity of which over fifty (including serotonin, acetylcholine, dopamine and norepinephrine) have been identified and described. Each of these traditional neurotransmitters has a relatively finite localization of function and neuroanatomy in the human nervous system. Acetylcholine, for example, is known to be the predominant traditional neurotransmitter in the neo-cortex and cortex. So too with dopamine/dopa in the basal ganglia, substantia nigra and nigro-striatal pathways; serotonin in the brain stem, reticular formation and nucleus of Raphe; and norepinephrine in the brain stem and locus ceruleus. Acetylcholine and serotonin are known to play important functional roles in the peripheral neurocutaneous system.

The second agent for effective neurotransmission is nitric oxide/cyclic-GMP (c-GMP), which appears to be conserved, in the same fashion, throughout all formations and facets of the human nervous system. This co-modulator or co-neurotransmitter appears to interact with the traditional neurotransmitter at the level of the efferent neuron cell membrane, most likely through glyco-lipo-protein cell receptors. Further effect may possibly occur on an intracellular or synaptic level through gated channels, specific enzyme targets, microfilament arrays and cytokines.

The defects primarily responsible for the vast array of neurodegenerative diseases and disorders is not always clear and may, in fact, be varied. Whatever the mechanism, however, the cumulative effect is to interfere with effective neurotransmission and subsequent cascading system effects that are the essential functions of the human nervous system.

Without wishing to be bound by theory, the invention, in certain embodiments, is a combination of a chemical to increase c-GMP levels in the targeted neural synapse and network with a second chemical to increase the levels of the traditional neurotransmitter(s) in the same location. By mass action or kinetic effect, the result is to overcome the dulled and/or failing effective neurotransmission and subsequent cascade regardless of the original location or cause of the neurodegenerative process. In this manner, the failing neurotransmission and secondary cascades will essentially be overridden to function at a higher and more normal level of responsiveness. This reactivation of the failing neurotransmission system may, in fact, effect changes in neuron plasticity, regeneration and apoptosis.

Any medication suitable for increasing the synaptic concentrations of these traditional neurotransmitters and c-GMP may be used in the current invention in combination with a PI-5, including currently available medications.

For example, autopsy changes seen in patients with advanced dementia represent a final common pathway of initially reversible dysfunction in the cortex and neo-cortex, the cognitive areas of the human brain, and that the proposed pharmaceutical combination effects 'neuro-restoration' of neurosynaptic defects in these areas (and, in the case of neuro-degenerative dementia incident to Parkinson's Disease, in the reticular formation and nucleus of Raphe as well.)

The PI-5 acts to increase nitric oxide levels in the above synapses, resulting in an activation of soluble Guanylate Cyclase in the synapse, and therefore an increase in the secondary messenger cyclic-GMP. The CI acts to increase the level of acetylcholine in the above synapses, a monoamine neurotransmitter. The SSRI acts to increase the levels of serotonin in the above synapses, another monoamine neurotransmitter.

The resulting increased cyclic-GMP acts in concert with the acetylcholine upon the efferent neuron receptor protein to correctly modulate the receptor's activity. This correct modulation, predominantly in the cortex and neo-cortex, corrects defective neuron synapse activation, and may also effect neuron regeneration and plasticity.

The increased cyclic-GMP will also act in concert with the serotonin to correctly modulate the serotonin receptor activity in the reticular complex and Nucleus of Raphe. Corrected neuron synapse activation in this area is then passed upward to the cortex and neo-cortex.

Without wishing to be bound by theory, in another embodiment, the invention itself is directed to a pharmaceutical composition and/or a treatment regime consisting of the administration of three medications, one to increase the synaptic concentration of serotonin, one to increase the synaptic concentration of acetylcholine, and one to increase the synaptic concentration of cyclic-GMP.

By "phosphodiesterase-5 inhibitor (PI-5)" is meant a substance or compound that inhibits (e.g., prevents or decreases) the catalytic activity of the phosphodiesterase isoenzyme (P-5). The enzyme P-5 catalyzes the breakdown of the smooth muscle relaxing agent cyclic guanosine monophosphate (cGMP). Typically, an inhibitor is a small molecule (e.g., MW less than about 1000) that binds to an enzyme at its active site or at another site to block the normal activity of the enzyme. Binding may be covalent, ionic, or via hydrogen bonding, or a combination of these, and may be reversible or irreversible.

Those of skill in the art will recognize that many compounds exist which are PI-5 inhibitors. Examples include, but are not limited to, sildenafil (VIAGRA®), vardenafil (LEVITRA®), tadalafil (CIALIS®), zaprinast, and the like. In one embodiment of the present invention, the PI-5 that is employed in the practice of the present invention is sildenafil. In another embodiment of the invention, the PI-5 is vardanefil. In yet another embodiment, the PI-5 is tadalafil.

In certain aspects of the present invention, the composition may include one or more PI-5, e.g., two PI-5s, three PI-5s and the like.

In certain aspects of the present invention, the PI-5 is administered in combination with at least one selective serotonin reuptake inhibitor (SSRI). SSRIs affect the chemicals that nerves in the brain use to send messages to one another. These chemical messengers, called neurotransmitters, are released by one nerve and taken up by other nerves. Neurotransmitters that are not taken up by other nerves are taken up by the same nerves that released them. This process is termed "reuptake." SSRIs work by inhibiting the reuptake of serotonin, an action which allows more serotonin to be available to be taken up by other nerves.

SSRIs which may be administered in combination with the PI-5 according to the present invention, include but are not limited to the following: paroxetine (PAXIL®), fluoxetine (PROZAC®), sertraline (ZOLOFT®), citalopram (CELEXA®), clovoxamine, escitalopram, femoxetine, flesinoxan, fluvoxamine (LUVOX®), trazodone, zimeldine, escitalopram (LEXAPRO®), alaproclate, nefazodone (SERZONE®), dapoxetine, duloxetine, milnacipran, clomin-pramine, indapline, alaprolclate, cericlamine, ifoxetine, trazodone hydrochloride (DESYREL®), venlafaxine, imipramine, imipramine N-oxide, desipramine, pirandamine, dazepinil, nefopam, befuraline, fezolamine, cianoimi-pramine, litoxetine, cericlamine, seproxetine, WY 27587, WY 27866, imeldine, tiflucarbine, viqualine, bazinaprine, YM 922, S 33005, F 98214-TA, OPC 14523, alaproclate, cyanodothepine, trimipramine, quinupramine, dothiepin, amoxapine, nitroxazepine, McN 5652, McN 5707, VN 2222, L 792339, roxindole, YM 35992,0177, Org 6582, Org 6997, Org 6906, amitriptyline, amitriptyline N-oxide, nortriptyline, CL 255.663, pirlindole, indatraline, LY 113.821, LY 214.281, CGP 6085 A, RU 25.591, napamezole, diclofensine, EMD 68.843, BMY 42.569, NS 2389, sercloremine, nitroqui-pazine, ademethionine, sibutramine, clovoxamine and those disclosed in U.S. Pat. No. 6,365,633; and PCT Patent Publication No. WO 01/27060.

In certain embodiments, the SSRI is LUVOX® (fluvoxamine). In other embodiments, the SSRI is Prozac® (fluoxetine). In another embodiment, the SSRI is CELEXA® (citalopram). In another embodiment, the SSRI is ZOLOFT® (sertraline). In yet another embodiment, the SSRI is PAXIL® (paroxetine).

In certain aspects of the present invention, the composition may include one or more SSRIs, e.g., two SSRIs, three SSRIs and the like.

In certain aspects of the present invention, the PI-5 is administered in combination with at least a Serotonin-norepinephrine reuptake inhibitor (SNRI). SNRIs selectively prevent the uptake of the neurotransmitters norepinephrine and serotonin, but exert no action on the neurotransmitter dopamine.

Suitable SNRIs that may be used in the present invention, include but are not limited to, atomoxetine, reboxetine venlafaxine (EFFEXOR® XR or EFFEXOR®), duloxetine (CYMBALTA®), desvenlafaxine (PRISTIQ®), sibutramine (MERIDIA®, Reductil REDUCTIL®), nefazodone (SERZONE®), milnacipran (DALCIPRAN® or IXEL®), and desipramine (NORPRAMIN® or PERTOFRANE®).

In certain embodiments, the SNRI is EFFEXOR® (venlafaxine). In other embodiments, the SSRI is CYMBALTA® (duloxetine).

In certain aspects of the present invention, the composition may include one or more SNRIs, e.g., two SNRIs, three SNRIs and the like.

In certain aspects of the present invention, the PI-5 is administered in combination with at least a Cholinesterase Inhibitor (CI). A "choline esterase inhibitor" is a compound that inhibits or reduces the activity of acetylcholinesterase or butyrylcholinesterase. CIs which may be administered in combination with the PI-5 according to the present invention include but are not limited to the following: tacrine (COGNEX®), donepezil (ARICEPT®), rivastigmine (EXELON®) galantamine (REMINYL®), donepezil hydrochloride, metrifonate, physostigmine, Huperzine A, physostigmine, heptylphysostigmine, phenserine, tolserine, cymserine, thiatolserine, distigmine bromide, thiacymserine, neostigmine, dichlorvos, phenethylnorcymserine, ganstigmine, epastigmine, pyridostigmine, citicoline, velnacrine, heptastigmine, edrophonium, TAK-147 (i.e., 3-[1-(phenylm-ethyl)-4-piperidinyl]-1-(2,3,4,5-tetrahydro-1H-1-benza-zepin-8-yl)-1-propanone fumarate or other salts thereof), T-82, upreazine, and the like.

In certain embodiments, the CI is COGNEX® (tacrine). In other embodiments, the CI is ARICEPT® (donepezil).

In certain aspects of the present invention, the composition may include one or more CIs, e.g., two CIs, three CIs and the like.

In certain aspects of the present invention, the PI-5 is administered in combination with at least any suitable agent that increases effective dopamine levels in the appropriate neural synapse. Dopamine agonists which may be administered in combination with the PI-5 according to the present invention, include but are not limited to, the following: bromocriptine (PARLODEL®), carbidopa/levodopa (SINEMET®), pramipexole (MIRAPEX®), cabergoline (DOSTINEX®), pergolide (PERMAX®), rotigotine (NEUPRO®), apomorphine (APOKYN®), ropinirole hydrochloride (Requip), testosterone, cocaine, strychnine, memantine, ARICEPT® (donepezil), amantadine, lisuride, ER-230, doprexin, docarpamine, terguride, levodopa, spheramine, romergoline, carmoxirole, zelandopam, sumanirole, sibena-det, quinpirole, quinelorane, talipexole, roxindole, a 4-alky-lamino-2(3H)-indolone compound, SKF38393, SKF83959, SKF81297, SKF77434, SKF75670, SKF82958, dihydrexi-dine, dinapsoline, A-77636, ABT-431, CY208-243, and A-68930.

In certain embodiments, the DI is bromocryptine. In other embodiments, the DI SINEMET® (carbidopa-levodopa). In another embodiment, the DI is MIRAPEX® (pramipexole).

In certain aspects of the present invention, the composition may include one or more DIs, e.g., two DIs, three DIs and the like.

In certain aspects of the present invention, the PI-5 is administered in combination with at least any suitable agent that increases the chemical concentrations of other neurotransmitters, such as amino acids, monoamines, neuropeptides and other agents capable of primary neurotransmission in the synaptic clefts (OI). Suitable OIs which may be administered in combination with the PI-5 according to the present invention include but are not limited to the following: epinephrine, norepinephrine, dopamine, serotonin, melatonin, glutamic acid, gamma aminobutyric acid, aspartic acid, glycine, adenosine, ATP, GTP, vasopressin, somatostatin, neurotensin, leuteinizing hormone, insulin, histamine, nitrogen monoxide, carbon monoxide, acetylcholine, octopamine, tyramine, gastrin, cholecystokinin, oxytocin, neurophysin I, neurophysin II, neuropeptides Y, pancreatic polypeptide, peptide YY, corticotrophin, dynorphin, endorphin, enkephaline, secretin, motilin, glucagons, vasoactive intestinal peptide, growth hormone releasing factor, neurokinin A, neurokinin B, substance P, bombesin, gastrin releasing peptide, and anandamide.

In certain aspects of the present invention, the composition may include one or more OIs, e.g., two OIs, three OIs and the like.

In certain embodiments, the composition of the present invention comprises one PI-5, one SSRI, and one CI.

In certain embodiments, the composition of the present invention comprises one PI-5, one SSRI, one CI and one DI.

In addition, by combining the agents according to the present invention, each reduces the side effects of the other agent and both contribute to the pharmacology efficacy for treating neurodegenerative diseases. In other aspects, by combining the agents according to the present invention, one agent may reduce the side effect of one other agent or two other agents or as many agents as present in the subject compositions. In another aspect, only one agent's side effects may be reduced as a result of the combination of agents.

As such, the current invention is directed to a new method and composition for the treatment of neurodegenerative diseases and skin damage by administering a combination of a PI-5 with one or more medications to increase target neurotransmitters including, without limitation, an SSRI, a SNRI, a CI, an NI, a DI or an OI.

Dosages, Formulations and Administration:

The combination of a PI-5 with one or more medications to increase target neurotransmitters including, without limitation, SSRIs, SNRIs, CIs, NIs, DIs or OIs provides increased therapeutic effects, and reduced adverse effects, making these pharmaceutical combinations extremely effective therapeutics, especially in the treatment of neurodegenerative diseases and the facilitation and acceleration of wound, burn and scar healing and for the maintenance and improvement of skin and mucous membrane health. Therapeutic levels of the combined drugs will vary from individual to individual and from disease to disease. The combination of PI-5 and traditional neurotransmitter augmentation medications in the appropriate amounts and intervals effective to treat any particular neurodegenerative disease will necessarily be monitored both clinically and chemically by the family practitioner, internist or neurologist. The relevant formulation can eventually take the form of a combined pill given daily, a daily or weekly patch, a long-term injection, an implant, or a short-acting form of medication.

The choice of appropriate dosages for the drugs used in combination therapy according to the present invention can be determined and optimized by the skilled artisan, e.g., by observation of the patient, including the patient's overall health, the response to the combination therapy, and the like. Optimization, for example, may be necessary if it is determined that a patient is not exhibiting the desired therapeutic effect or conversely, if the patient is experiencing undesirable or adverse side effects that are too many in number or are of a troublesome severity.

In one embodiment, each component of the combination (e.g., PI-5 with one or more SSRIs, SNRIs, CIs, NIs, DIs or OIs) is prescribed at a dose that is below the typically described dose for each component as a monotherapy. The components may be prescribed separately or as a combination dosage. In one embodiment, each component of the combination (e.g., PI-5 with one or more SSRIs, SNRIs, CIs, NIs, DIs or OIs) is prescribed at a dose that is below the typically described dose for each component as a monotherapy. In another embodiment, each component of the combination (e.g., PI-5 with one or more SSRIs, SNRIs, CIs, NIs, DIs or OIs) is prescribed at a dose that is above the typically described dose for each component as a monotherapy. The components may be prescribed separately or as a combination dosage.

In another embodiment, the prescribed dosage of the PI-5 is above the typically described dose for monotherapy, and the one or more of an SSRI, a SNRI, a CI, an NI, a DI or an OI is prescribed at a dosage that is at or below the typically described dose for monotherapy. In another embodiment, the prescribed dosage of the PI-5 is at or below the typically described dose for monotherapy, and the one or more SSRIs, SNRIs, CIs, NIs, DIs or OIs is prescribed at a dosage that is above the typically described dose for monotherapy. In certain embodiments, the prescribed dosage of the PI-5 and the prescribed dosage of the one or more SSRIs, SNRIs, CIs, NIs, DIs or OIs are described each at either higher or lower dosages than is typically described for each component a monotherapy.

In certain embodiments, the PI-5 may be, for example, administered from 2-400 mg per day, including from 2-200, and including from 2-100 mg per day. In one aspect, the PI-5 is administered from 2-85 mg per day, including from 2-80, and including from 5-80, and including from 10-80, and including from 5-70 mg per day.

In certain embodiments, when CIALIS® (tadalafil) is the PI-5, CIALIS® (tadalafil) may be, for example, administered from 2-120 mg per day, including from 4-70 mg per day. In one aspect, CIALIS® (tadalafil) is administered from 5-60 mg per day.

In certain embodiments, when LEVITRA® (vardenafil) is the PI-5, LEVITRA® (vardenafil) may be, for example administered from 2-100 mg per day, including from 4-90 mg per day. In one aspect, LEVITRA® (vardenafil) is administered from 5- 80 mg per day.

In certain embodiments, when VIAGRA® (sildenafil) is the PI-5, VIAGRA® (sildenafil) may be, for example administered from 5-400 mg per day, including from 7.5-250 mg per day. In one aspect, VIAGRA® (sildenafil) is administered from 10-200 mg per day.

In certain embodiments, the SSRI may be, for example, administered from 5-600 mg per day, including from 5-400, and including from 10-400, including from 25-400 mg per day. In one aspect, the SSRI is administered from 5-200 mg per day, including from 50-200, and including from 10-80, and including from 10-50, and including from 10-20 mg per day.

In certain embodiments, when LUVOX® (fluvoxamine) is the SSRI, LUVOX® (fluvoxamine) may be, for example, administered from 5-600 mg per day. In one aspect, the LUVOX® (fluvoxamine) is administered from 10-400 mg per day.

In certain embodiments, when PROZAC® (fluoxetine) is the SSRI, PROZAC® (fluoxetine) may be, for example administered from 5-200 mg per day. In one aspect, PROZAC® (fluoxetine) is administered from 10-80 mg per day.

In certain embodiments, when CELEXA® (citalopram) is the SSRI, CELEXA® (citalopram) may be, for example administered from 5-100 mg per day. In one aspect, CELEXA® (citalopram) is administered from 10-20 mg per day.

In certain embodiments, when ZOLOFT® (sertraline) is the SSRI, ZOLOFT® (sertraline) may be, for example administered from 25-400 mg per day. In one aspect, ZOLOFT® (sertraline) is administered from 50-200 mg per day.

In certain embodiments, when PAXIL® (paroxetine) is the SSRI, PAXIL® (paroxetine) may be, for example administered from 5-200 mg per day. In one aspect, PAXIL® (paroxetine) is administered from 10-80 mg per day.

In certain embodiments, the SNRI may be, for example, administered from 5-500 mg per day, including from 5-300, and including from 7-250 mg per day. In one aspect, the SNRI is administered from 20-200 mg per day.

In certain embodiments, when EFFEXOR® (venlafaxine) is the SNRI, EFFEXOR® (venlafaxine) may be, for example, administered from 5-500 mg per day. In one aspect, the EFFEXOR® (venlafaxine) is administered from 10-400 mg per day, including from 25-300 and from 50-200 mg per day.

In certain embodiments, when CYMBALTA® (duloxetine) is the SNRI, CYMBALTA® (duloxetine) may be, for example, administered from 10-400 mg per day. In one aspect, CYMBALTA® (duloxetine) is administered from 20-200 mg per day.

In certain embodiments, the CI may be, for example, administered from 5-200 mg per day, including from 10-200, and including from 10-120. In one aspect, the CI is administered from 5-120, including from 10-120, including from 5-100 mg per day. In another aspect, the SSRI is administered from 10-20 mg per day.

In certain embodiments, when COGNEX® (tacrine) is the CI, COGNEX® (tacrine) may be, for example, administered from 5-200 mg per day. In one aspect, COGNEX® (tacrine) is administered from 10-120 mg per day.

In certain embodiments, when ARICEPT® (donepezil) is the CI, ARICEPT® (donepezil) may be, for example, administered from 5-100 mg per day. In one aspect, the ARICEPT® (donepezil) is administered from 10-20 mg per day.

In certain embodiments, the DI may be, for example, administered from 0.125-80 mg per day, including from 0.125-40. In another aspect, the DI is administered from 0.125-9 mg per day.

In certain embodiments, when bromocryptine is the DI, bromocryptine may be, for example, administered from 2.5-80 mg per day. In one aspect, the bromocryptine is administered from 2.5-20 mg per day.

In certain embodiments, when SINEMET® (carbidopa-levodopa) (25/100) is the DI, SINEMET® (carbidopa-levodopa) may be, for example, administered from 2 tabs-40 tabs per day. In one aspect, the SINEMET® (carbidopa-levodopa) is administered from 2 tabs-40 tabs per day.

In certain embodiments, when MIRAPEX® (pramipexole) is the DI, MIRAPEX® (pramipexole) may be, for example, administered from 0.125-40 mg per day. In one aspect, the MIRAPEX® (pramipexole) is administered from 0.125-9 mg per day.

In certain embodiments, any suitable medication to increase the chemical concentrations of other neurotransmitters, such as amino acids, monoamines, neuropeptides and other agents capable of primary neurotransmission in the synaptic clefts are also administered accordingly.

Further, the patient may receive the specific dosage over a period of weeks, months, or years. For example, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years and the like.

In some embodiments, an "effective amount" of the combination therapy is an amount that results in a reduction of at least one pathological parameter associated with a neurodegenerative disease or skin damage. Thus, e.g., in some embodiments, an effective amount of the combination therapy is an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the expected reduction in the parameter associated with a monotherapeutic regime or with no treatment at all.

When administered in separate formulations, the PI-5 with one or more SSRIs, SNRIs, CIs, NIs, DIs or OIs may be administered substantially simultaneously (e.g., within about 60 minutes, about 50 minutes, about 40 minutes, about 30 minutes, about 20 minutes, about 10 minutes, about 5 minutes, or about 1 minute of each other) or separated in time by about 1 hour, about 2 hours, about 4 hours, about 6 hours, about 10 hours, about 12 hours, about 24 hours, about 36 hours, or about 72 hours, or more.

It is especially advantageous to formulate compositions of the invention in unit dosage form for ease of administration and uniformity of dosage. The specifications of the novel dosage unit forms of the invention are dependent on the unique characteristics of the composition containing the PI-5 with one or more SSRIs, SNRIs, CIs, NIs, DIs or OIs and the particular therapeutic effect to be achieved. Dosages can further be determined by reference to the usual dose and manner of administration of the ingredients. It is also within the scope of the present invention to formulate a single physically discrete dosage form having each of the active ingredients of the combination treatment (e.g., a single dosage form having a PI-5 with one or more SSRIs, SNRIs, CIs, NIs, DIs or OIs).

The method of administration of compositions or combinations of the invention will depend, in particular, on the type of PI-5 used and the chosen one or more SSRIs, SNRIs, CIs, NIs, DIs or OIs. The PI-5 and the one or more SSRIs, SNRIs, CIs, NIs, DIs or OIs may be administered together in the same composition or simultaneously or sequentially in two separate compositions. Also, one or more PI-5 or one or more SSRIs, SNRIs, CIs, NIs, DIs or OIs may be administered to a subject or patient either in the form of a therapeutic composition or in combination, e.g., in the form of one or more separate compositions administered simultaneously or sequentially. The schedule of administration will be dependent on the type of PI-5 and SSRIs, SNRIs, CIs, NIs, DIs or OIs chosen. For example, one or more of the PI-5(s) and one or more of the SSRIs, SNRIs, CIs, NIs, DIs or OIs can have a stimulant effect and the degree of such stimulant effect may vary depending on the particular agents chosen. Accordingly, one or more of the PI-5s, SSRIs, SNRIs, CIs, NIs, DIs or OIs may have a significant stimulant effect and therefore, might be administered earlier in the day than administration of one or more of the PI-5s, SSRIs, SNRIs, CIs, NIs, DIs or OIs having a lesser stimulant effect. Likewise, one or more of the PI-5s, SSRIs, SNRIs, CIs, NIs, DIs or OIs can have a sedative effect and the degree of such sedative effect may vary depending on the agent chosen. Accordingly, one or more of the PI-5s, SSRIs, SNRIs, CIs, NIs, DIs or OIs having a significant sedative effect might be administered later in the day than administration of an agent having a lesser sedative effect. Moreover, one or more of the PI-5s, SSRIs, SNRIs, CIs, NIs, DIs or OIs having lesser stimulant or sedative effects, respectively, may be administered simultaneously.

Administration of the active agent may be carried out using any appropriate mode of administration. Thus, administration can be, for example, oral, topical, parenteral, transdermal, transmucosal (including rectal, vaginal, and transurethral), sublingual, by inhalation, or via an implanted reservoir in a dosage form. The term "parenteral" as used herein is intended to include subcutaneous, intravenous, and intramuscular injection.

Depending on the intended mode of administration, the pharmaceutical formulation may be a solid, semi-solid or liquid, such as, for example, a tablet, a capsule, a caplet, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in *Remington: The Science and Practice of Pharmacy* (Easton, Pa.: Mack Publishing Co., 1995). For those compounds that are orally active, oral dosage forms are generally preferred, and include tablets, capsules, caplets, solutions, suspensions and syrups, and may also comprise a plurality of granules, beads, powders, or pellets that may or may not be encapsulated. Preferred oral dosage forms are tablets and capsules.

As noted above, it is especially advantageous to formulate compositions of the invention in unit dosage form for ease of administration and uniformity of dosage. The term "unit dosage forms" as used herein refers to physically discrete units suited as unitary dosages for the individuals to be treated. That is, the compositions are formulated into discrete dosage units each containing a predetermined, "unit dosage" quantity of an active agent calculated to produce the desired therapeutic effect in association with the required pharmaceutical carrier. The specifications of unit dosage forms of the invention are dependent on the unique characteristics of the active agent to be delivered. Dosages can further be determined by reference to the usual dose and manner of administration of the ingredients. It should be noted that, in some cases, two or more individual dosage units in combination provide a therapeutically effective amount of the active agent, e.g., two or more tablets or capsules taken together may provide a therapeutically effective dosage of the PI-5s and SSRIs, SNRIs, CIs, NIs, DIs or OIs chosen such that the unit dosage in each tablet or capsule is approximately 50% of the therapeutically effective amount.

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like.

Capsules are also preferred oral dosage forms for those pharmaceutical active agents that are orally active, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, *Remington: The Science and Practice of Pharmacy*, cited earlier herein, which describes materials and methods for preparing encapsulated pharmaceuticals.

Oral dosage forms, whether tablets, capsules, caplets, or particulates, may, if desired, be formulated so as to provide for controlled release of the PI-5s and SSRIs, SNRIs, CIs, NIs, DIs or OIs chosen, and in a preferred embodiment, the present formulations are controlled release oral dosage forms. Generally, the dosage forms provide for sustained release, i.e., gradual, release of the PI-5s and SSRIs, SNRIs, CIs, NIs, DIs or OIs from the dosage form to the patient's body over an extended time period, typically providing for a substantially constant blood level of the agent over a time period in the range of about 4 to about 12 hours, typically in the range of about 6 to about 10 hours. In a particularly preferred embodiment, there is a very gradual increase in blood level of the drug following oral administration of the dosage form containing the PI-5s and SSRIs, SNRIs, CIs, NIs, DIs or OIs such that peak blood level is not reached until at least 4-6 hours have elapsed, with the rate of increase of blood level drug approximately linear. In addition, in the preferred embodiment, there is an equally gradual decrease in blood level at the end of the sustained release period.

Generally, as will be appreciated by those of ordinary skill in the art, sustained release dosage forms are formulated by dispersing the active agent within a matrix of a gradually hydrolyzable material such as a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preferred sustained release dosage forms herein are composed of the acrylate and methacrylate copolymers available under the tradename "Eudragit" from Rohm Pharma (Germany). The Eudragit series E, L, S, RL, RS, and NE copolymers are available as solubilized in organic solvent, in an aqueous dispersion, or as a dry powder. Preferred acrylate polymers are copolymers of methacrylic acid and methyl methacrylate, such as the Eudragit L and Eudragit S series polymers. Particularly preferred such copolymers are Eudragit L-30D-55 and Eudragit L-100-55 (the latter copolymer is a spray-dried form of Eudragit L-30D-55 that can be reconstituted with water). The molecular weight of the Eudragit L-30D-55 and Eudragit L-100-55 copolymer is approximately 135,000 Da, with a ratio of free carboxyl groups to ester groups of approximately 1:1. The copolymer is generally insoluble in aqueous fluids having a pH below 5.5. Another particularly suitable methacrylic acid-methyl methacrylate copolymer is Eudragit S-100, which differs from Eudragit L-30D-55 in that the ratio of free carboxyl groups to ester groups is approximately 1:2. Eudragit S-100 is insoluble at pH below 5.5, but unlike Eudragit L-30D-55, is poorly soluble in aqueous fluids having a pH in the range of 5.5 to 7.0. This copolymer is soluble at pH 7.0 and above. Eudragit L-100 may also be used, which has a pH-dependent solubility profile between that of Eudragit L-30D-55 and Eudragit S-100, insofar as it is insoluble at a pH below 6.0. It will be appreciated by those skilled in the art that Eudragit L-30D-55, L-100-55, L-100, and S-100 can be replaced with other acceptable polymers having similar pH-dependent solubility characteristics. Other preferred Eudragit polymers are cationic, such as the Eudragit E, RS, and RL series polymers. Eudragit E100 and E PO are cationic copolymers of dimethylaminoethyl methacrylate and neutral methacrylates (e.g., methyl methacrylate), while Eudragit RS and Eudragit RL polymers are analogous polymers, composed of neutral methacrylic acid esters and a small proportion of trimethylammonioethyl methacrylate.

Preparations according to this invention for parenteral administration include sterile aqueous and nonaqueous solutions, suspensions, and emulsions. Injectable aqueous solutions contain the active agent in water-soluble form. Examples of nonaqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable formulations are rendered sterile by incorporation of a sterilizing agent, filtration through a bacteria-retaining filter, irradiation, or heat. They can also be manufactured using a sterile injectable medium. The active agent may also be in dried, e.g., lyophilized, form that may be rehydrated with a suitable vehicle immediately prior to administration via injection.

The active agent may also be administered through the skin using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

In addition to the formulations described previously, the active agent may be formulated as a depot preparation for controlled release of the active agent, preferably sustained release over an extended time period. These sustained release dosage forms are generally administered by implantation (e.g., subcutaneously or intramuscularly or by intramuscular injection).

In another aspect, the combination therapy of the present invention may be a topical formulation. In accordance with the subject invention, an effective or optimal amount of the combination of PI-5 with SSRIs, SNRIs, CIs, NIs, DIs or OIs as a topical formulation is applied to a skin surface. As will be apparent to those of skill in the art, the effective or optimal amount will vary depending on the particular combination of agent employed, the particular disease state or condition being treated, etc. The topical formulation may be applied to any convenient topical site. Topical sites of interest include, but are not limited to: arms, legs, face, neck, torso, etc. Application may be accomplished in any convenient manner and may be dictated at least in part by the form of the topical formulation, i.e., whether the topical formulation is present as a cream, lotion, ointment, gel, solution, foam, powder, etc., the container holding the formulation, etc. For example, the topical formulation may be sprayed onto a skin surface, rolled-onto a skin surface, or a subject may apply the topical formulation using a swab, finger, and the like. Other protocols for applying a topical formulation are known to those of skill in the art and may be employed in accordance with the subject methods.

Although the present compositions will generally be administered orally, parenterally, transdermally, topically, or via an implanted depot, other modes of administration are suitable as well. For example, administration may be transmucosal, e.g., rectal or vaginal, preferably using a suppository that contains, in addition to the active agent, excipients such as a suppository wax. Transmucosal administration also encompasses transurethral administration, as described, for example, in U.S. Pat. Nos. 5,242,391, 5,474,535, and 5,773,020 to Place et al. Formulations for nasal or sublingual administration are also prepared with standard excipients well known in the art. The pharmaceutical compositions of the invention may also be formulated for inhalation, e.g., as a solution in saline, as a dry powder, or as an aerosol.

Indications:

Neurodegenerative Diseases

While the invention is useful in conjunction with numerous pharmaceutical agents and therapeutic regimens, conditions of particular interest include neurodegenerative diseases such as Alzheimer's disease, Parkinson's disease, multiple sclerosis, amyotrophic lateral sclerosis, fronto-temporal dementia with Parkinson's features, progressive supranuclear palsies, essential dyskinesias and dementia.

The combination of at least one PI-5 with one or more medications to increase target neurotransmitters including, without limitation, SSRIs, SNRIs, CIs, NIs, DIs or OIs provide increased therapeutic effects, and reduced adverse effects, making these pharmaceutical combinations extremely effective therapeutics, especially in the treatment of neurodegenerative diseases. Subjects suitable for treatment with the subject combination therapy treatment regimen include individuals suffering from the following conditions associated with neurodegenerative diseases.

Parkinson's Disease

Parkinson's disease is a chronic and progressive neurodegenerative movement disorder that persists over a long period of time as symptoms continue to worsen. The disease was first described by a London physician named Dr. James Parkinson.

Parkinson's is caused by the gradual malfunctioning and cell loss in substantia nigra, the main dopamine producer in the brain. This neurotransmitter is believed to be responsible for sending information to different parts of the brain in charge of movement control and coordination. Decreased dopamine production slows down the process of sending messages from the brain to different organs, disrupting the individual's ability to control and initiate any movement.

The 3 key signs of Parkinson disease are tremor (shaking) at rest, rigidity, and slowness in the initiation of movement (called bradykinesia). Of these features, 2 are required to make the diagnosis. Postural instability is the fourth key sign, but it happens late in the disease, usually after having PD 8 years or more.

Tremor at rest usually begins in one arm and may start and stop. As with most tremors, it worsens when under stress and improves during rest or sleep. After several months to a few years, both arms may become affected, but the beginning asymmetry (lopsidedness) is often maintained. PD tremor may also involve the tongue, lips, or chin. The characteristic PD tremor is present and most prominent with the limb at rest. The tremor may appear as a pill-rolling motion of the hand or a simple oscillation of the hand or arm.

Rigidity refers to an increase in resistance to someone else moving your joint. The resistance can be either smooth (lead-pipe) or start and stop (cog wheeling). (Cog wheeling is thought to be a tremor rather than rigidity.) Having someone else flex and extend your relaxed wrists tests for rigidity. Rigidity can be made more obvious with voluntary movement in the opposite limb.

Bradykinesia refers to slowness of movement but also includes a lessening of unplanned movements and decreased size of movement. Bradykinesia is also expressed as micrographia (small handwriting), hypomimia (decreased facial expression), decreased blink rate, and hypophonia (soft speech).

Postural instability refers to imbalance and loss of reflexes used to keep you upright. This symptom is an important milestone, because it is not easy to treat and a common source of disability in late disease.

Other symptoms include freezing when starting to walk (start-hesitation), during turning, or crossing a threshold such as going through a doorway, flexed postures of neck, trunk, and limbs may occur, altered mental status generally occurs late in PD and affects 15-30% of people with PD, short-term memory and visio-spacial function may be impaired.

The onset of PD is typically lopsided, with the most common initial finding being an asymmetric rest tremor in one arm. About 20% of people first experience clumsiness in 1 hand.

The best clinical predictors of a diagnosis of PD are asymmetry, the presence of rest tremor, and a good response to dopamine replacement therapy.

Parkinson's affects all individuals regardless of their gender, economic, geographic and social status. However, men are at a slightly greater risk of developing the disease. In addition, certain studies also indicate Caucasians are more prone to the disease compared to African-Americans and Asians. Age is the ultimate determinant of the disease. The older a person is, the more likely he/she is to develop the disease; however, several cases of Parkinson's in individuals younger than 40 years have been reported.

Alzheimer's Disease (AD)

Alzheimer's Disease (AD), the most common cause of dementia, is a collection of brain disorders, usually in older people, characterized by slow progressive loss of brain function, especially notable by lapses in memory, disorientation, confusion, mood swings, changes in personality, language problems, such as difficulty in finding the right words for everyday objects, loss of behavioral inhibitions, loss of motivation, and paranoia. The prognosis and course of AD varies widely, and the duration of illness can be a few years up to over 20 years in duration. During this time parts of the brain that control memory and thinking are first affected, followed by other brain changes that ultimately result in brain cell death.

AD is characterized by distinct neuropathological changes in the brain. Among the most notable are the appearance of plaques and tangles of neurofibrils within brain nerves that affect nerve synapses and nerve-nerve cell communication.

AD affects mainly people aged 60 years or older. The risk of developing AD continues to increase with age. People aged 80 years, for example, have a significantly greater risk than people aged 65 years. About 5 million people in the United States and more than 30 million people worldwide have AD. Many others have mild, or minimal, cognitive impairment, which frequently precedes dementia.

The number of people with AD is expected to rise substantially in the next few decades because of the aging of the population. The disease affects all races and ethnic groups and seems to affect more women than men.

AD is a progressive disease, which means that it gets worse over time. It cannot be cured or reversed by any known treatment. The symptoms often are subtle at first.

Over time, people with the disease lose their ability to think and reason clearly, judge situations, solve problems, concentrate, remember useful information, take care of themselves, and even speak and changes in behavior and personality are common.

People with mild AD usually require close supervision and help with everyday tasks such as cooking, shopping, and paying bills. People with severe AD can do little on their own and require complete full-time care. Because of this, AD is considered a major public health problem. The cost of caring for people with the disease is estimated at over $100 billion per year in the United States. The average yearly cost per affected person is $20,000 to $40,000, depending on the severity of the disease. That cost doesn't take into account the loss of quality of life for the affected person, nor the physical and emotional toll on family caregivers.

Amyothrophic Lateral Sclerosis (ALS)

ALS, also known as Lou Gehrig's Disease, is a progressive neurodegenerative disease of the upper and lower motor neurons located in the mid-brain, brainstem and spinal cord. In ALS the motor neurons in these areas become dysfunctional and slowly die, and when this occurs the muscles can no longer receive nerve impulses from the brain. The muscles then weaken and atrophy, resulting eventually in muscle paralysis. ALS is characterized by a rapidly progressive degeneration of motor neurons in the brain and spinal chord, which ultimately leads to paralysis and premature death. Overall, the prevalence of ALS is low (approximately 5 in 100,000 individuals), but incidence increases with age, showing a peak between 55 and 75 years ALS patients progress rather quickly, and only 5% of ALS patients survive beyond 5 years after their diagnosis. The diagnosis of ALS is performed by neurologists and generally follows a set of signs and symptoms, but there are atypical ALS cases that do not follow the usual clinical course and do not show all of the typical signs and symptoms of classical ALS.

ALS may begin as weakness, awkwardness, or atrophy in one or more limbs. It may start as a difficulty swallowing or speaking. The symptoms may be very subtle at first, and may be overlooked. Common symptoms include the following: difficulty standing, walking, or running, clumsiness—frequent tripping or falls, difficulty with fine hand motions such as buttoning, writing, turning a key in a lock, atrophy of hand muscles, atrophy of tongue, difficulty chewing food, difficulty swallowing (dysphagia), difficulty speaking, oversensitive gag reflex, difficulty forming words (dysarthria), weakness and atrophy in specific muscles, tight, stiff muscles (spasticity), muscle cramps, and muscle twitching visible under skin (fasciculations).

There may be evidence for frontal lobe dysfunction in patients with ALS. Usually, this dysfunction is subclinical (not readily apparent or causing symptoms) and it is detectable only when looked for specifically with focused tests. However, in a minority of patients, clinically significant cognitive impairment becomes evident, with a continuum of abnormalities extending all the way to frank frontotemporal dementia. In addition to difficulties in planning and sequencing (the most common manifestations of "executive dysfunction" due to frontal lobe disease) some patients may express an otherwise inexplicable nonchalance or lack of insight into their situation and its impact on themselves and their loved ones and others; fortunately rarely, they may become less friendly than their usual selves. These aspects of ALS, when present, may pose major challenges to caregivers and healthcare personnel alike, and they may be associated with shorter survival.

Depression and anxiety may occur in patients with ALS. Though difficult to prove, these are likely part of the disease process itself, rather than mere reactions of the patients to their condition. Depression and anxiety are treatable. Finally, some patients with ALS frequently exhibit a so-called pseudobulbar affect, manifesting as involuntary, uncontrolled outbursts of crying or laughter, which is distinct from their underlying mood.

As the disease progresses, the person with ALS loses the ability to carry out everyday activities such as dressing, eating, and working. Eventually getting out of bed becomes impossible without assistance. The person becomes restricted to a wheelchair or bed (the development of bedsores can be a problem.) As the respiratory muscles weaken, breathing becomes more and more difficult. The risk of pneumonia increases.

ALS is diagnosed in about 5,000 people each year in the United States, where about 20,000 people are believed to have the condition. It affects all races and ethnic groups. The disease can occur at any age but is most common in people aged 40-60 years. Men are affected more often than women. No cure is available for ALS and the effects of the disease are not reversible.

Multiple Sclerosis (MS)

Multiple sclerosis is a disease of the nerves of the central nervous system, and it can occur in young as well as older people. The nerves in various parts of the brain are covered by a protective insulation made up of the protein myelin and other proteins imbedded in a lipid sheath so that the electrical impulses that cause nerve conduction are protected. In MS, inflammation and the presence of autoimmune antibodies against myelin and other antigens causes the protective sheath to break down and lose their protective capacity (demyelination), resulting in decrease or loss of electrical impulses along the nerve. In progressive MS the nerve cells are damaged by demyelination and deposition of plaques on the nerve cells to the point where nerve cell death occurs.

The signs and symptoms of MS include visual disturbances, muscle weakness, fatigue, numbness, difficulty in coordinating movement and balance, tremors, dizziness, loss of hearing, memory loss, impairment in judgment, behavioral changes and pain. The symptoms may cycle or relapse-remit initially and later on become progressive and degeneration occurs in a steady decline. MS may affect virtually any myelinated nerve, sensory or motorneuron, and it can cause widespread signs and symptoms.

The symptoms of multiple sclerosis can be different from person to person. Visual, sensory, and motor signs and symptoms are all part of multiple sclerosis. The clinical manifestations are varied, and therefore there is a wide range of symptoms that can appear. Some people have mild cases of multiple sclerosis with little or no disability over the years. Others have more severe types of multiple sclerosis, requiring confinement to a wheelchair or bed. Still others may live their entire lives symptom-free (some individuals without multiple sclerosis symptoms are found incidentally to have multiple sclerosis lesions by MRI, or individuals in whom an examination of their brain after death unexpectedly reveals that they were affected by the disease). This variability makes it difficult in some cases to diagnose multiple sclerosis. Often the signs and symptoms are mistaken as being psychiatric in origin.

Multiple sclerosis commonly affects the cerebellum, the portion of the brain responsible for balance and fine motor coordination. Consequently, people with multiple sclerosis often have difficulty maintaining their balance when walking and performing delicate tasks with their hands. Unexplained dropping of a cup or other object or unusual weakness can occur.

Patients may experience facial pain, a sensation of spinning referred to as vertigo, and sometimes hearing loss. Virtually any area of the body can be involved, making this disease the great imitator of other disorders of the nervous system. The patient may experience painful muscle spasms or loss of strength in one or more of the arms or legs. The nerve fibers that conduct touch, pain, and temperature sensations are often affected, causing tingling, numbness or electrical-type pain sensations in the chest, abdomen, arms or legs.

Multiple sclerosis can involve the nerves responsible for involuntary actions of the bladder and intestines. The patient may often have constipation and urinary retention. These symptoms lead to other complications, such as infections of the bladder, kidney, or blood.

Most people with multiple sclerosis complain of a constant state of tiredness. Something as simple as carrying groceries up a flight of stairs may become an impossible task for someone with multiple sclerosis.

Multiple sclerosis is more common in individuals of northern European descent. Women are more than twice as likely to develop multiple sclerosis as men. Multiple sclerosis usually affects people between the ages of 20 and 50 years, and the average age of onset is approximately 34 years.

Frontotemporal Dementia (FTD)

FTD is a heterogenous group of syndromes defined clinically by a gradual and progressive change in behavior and personal conduct and/or by a gradual and progressive language dysfunction. The initial symptoms typically occur without affecting other cognitive domains, such as memory, and rarely present with an onset age beyond 75 years. In some instances, deficits in behavior and language are also accompanied by parkinsonism or progressive motor neuron disease. Neuropathologically, FTD is caused by neurodegeneration in the frontal and/or temporal lobes.

The most common presentation is an early change in social and personal conduct, characterized by difficulty modulating behavior to the social demands of a situation. This is often associated with a lack of inhibition, resulting in impulsive or inappropriate behavior, such as swearing at inappropriate times, outbursts of frustration, or lack of social tact.

As the disease progresses, this may lead to frank criminal behavior (e.g. shoplifting), poor financial judgment or impulsive buying. At the extreme, the impulsivity can be self-destructive, as when patients try to get out of a moving car. In some individuals, inappropriate sexual behavior occurs.

There may also be repetitive or compulsive behaviors. This may include a preoccupation with repeating specific acts (e.g., reading the same book over and over) or repeating specific physical actions (e.g., walking to the same location repeatedly).

Dietary habits and personal hygiene may also change. Overeating is common as well as food fads in which only certain foods are eaten. There is a loss of concern for one's personal appearance and patients may be increasingly unkempt early in the course of disease.

All this occurs in the setting of the patient showing very little insight into or personal concern for their actions. Even though there are complaints of memory disturbance, these patients do not have a true amnestic syndrome. They are able to keep track of day to day events and to be oriented.

FTD affects an estimated 250,000 Americans or the prevalence of FTD among people ages 45 to 64 was estimated to be 6.7 per 100,000. The disease affects both sexes equally. About 40% of patients have a clear-cut family history. The mean duration of the illness is about eight years.

Progressive Supranuclear Palsies (PSP)

Progressive supranuclear palsies is a rare degenerative disease of the brain. The disease impairs movements and balance. Many people with PSP also experience changes in mood, behavior, and personality. A decline in cognitive mental processes, such as thinking, memory, attention, and speech, is not uncommon. When these mental changes are severe enough to interfere with everyday activities, they are called dementia.

PSP is progressive, meaning that it gets worse over time. The disease affects the part of the brain above the nuclei ("supranuclear"), which are pea-sized structures in the part of the nervous system that controls eye movements. Palsy means weakness, and it is this characteristic weakness in eye movements for which the disease is named.

The symptoms of PSP usually appear very slowly. Many people experience a prolonged phase of symptoms such as fatigue (feeling tired), headaches, joint pains, dizziness, and depression. Gradually, the following more specific symptoms appear: unexplained balance problems, stiff or awkward steps while walking, very slow movements, frequent falls, clumsiness, visual problems (blurry or double vision, problems controlling eye movements and inability to maintain eye contact), light sensitivity, behavior or personality changes, irritation, grouchiness, memory loss, forgetfulness, apathy (indifference), slowed thinking, reasoning, planning, inappropriate laughing or crying, angry or aggressive outbursts, slurred speech, swallowing problems, mask-like facial expression (no expression), muscle spasms, and inability to hold urine (incontinence).

About 20,000 people in the United States have PSP. The disease usually develops in people aged 60 years or older. Symptoms typically become noticeable in the early 60s, although the disease sometimes affects people in their 40s or 50s. PSP is slightly more common in men than in women.

Because PSP mainly affects older people and has somewhat similar symptoms, it is often mistaken for Parkinson disease, a much more common movement disorder. The distinction is important, because treatments that help many people with Parkinson disease do not help those with PSP.

Essential Dyskinesias

Dyskinesias are excessive abnormal movements that are involuntary. There are several different types of dyskinesias, and each has different clinical symptoms, causes, and treatments. Adults and children with certain chronic brain disorders often exhibit symptoms of dyskinesia. Movement can occur in the head, arms, legs, hand, feet, lips, or tongue. The dyskinesias can be categorized as chorea, dystonia, myoclonus, tremor, and paroxysmal tardive (late-onset type). Other forms of dyskinesia include athetosis, ballism, akathisia, tics, stereotypy, and restless legs. Dyskinesias can also be called hyperkinesia syndromes.

Choreas are abnormal movements that are irregular, involuntary, nonrhymical, abrupt, rapid, and nonsustained jerking, which continuously flow from one body part to another. Movements are isolated, brief, and infrequent. Chorea can cause inability to maintain a sustained contraction, which causes affected persons to drop objects. Persons with chorea have an irregular dance-like gait. The cause of chorea is not completely understood.

Dystonia that occurs at rest may persist as the kinetic (clonic) form. Dystonias can be either focal or generalized. Focal dystonias are involuntary movements in a single body part, which commonly includes blepharospasm (upper facial), spasmodic torticollis (cervical), and writer's cramp. Dystonia affecting two or more body regions is called segmental dystonia. Generalized dystonia typically affects the trunk, one or both legs, and another body part. Other types of dystonias include Merge's syndrome (spasms of the jaw muscles when opening and closing of the mouth). Spasmodic dystonias can cause speech impairment due to spasms of laryngeal (throat) muscles. The intensity of muscular movements in patients with dystonia can fluctuate, and symptoms worsen during fatigue, stress, activity, and change in posture. In some cases, the bizarre symptoms of dystonia can be mistaken for psychological illness. Dystonias can be inherited or acquired due to another primary cause. Inherited diseases that exhibit dystonia are rare and include dopa-responsive dystonia, idiopathic tension dystonia, and x-linked dystonia-Parkinsonism (found among Ashkenazi Jews).

Myoclonus refers to muscular contractions (positive myoclonus) that are brief, sudden, and severe, and shock-like movements or inhibitions (negative myoclonus). Myoclonus could be generalized or isolated. The movements consist of rhythmical irregular jerks or oscillatory jerks that occur abruptly and then fade. The abnormal jerks are associated with environmental stimuli such as light, sound, movement, and visual threat. The condition can be misdiagnosed for epilepsy. Myoclonus usually occurs at rest; but can also appear when the affected body part is subjected to voluntary activity, which is referred to as action myoclonus. Action myoclonus is more disabling than rest myoclonus.

Tremors are rhythmic oscillatory movements that are regular, but may vary in rate, location, amplitude, and constancy, and depend on type and severity of the tremor. Tremors can occur with action, at rest, and with holding a position or posture. The tremor can be so rapid it is often described as a "flicker of light." Subtypes of tremors include tremors at rest, essential tremor, which is a postural tremor at either rest or activity and may be inherited, or tremor with movement (intention "kinetic" tremor). Resting tremors are usually slow, occur during an activity, and disappear when action is initiated (e.g., Parkinson's disease). Essential tremor is usually benign, but can cause disability due to impairment of handwriting and limitations of activities related to daily living. Essential tremor may be inherited.

Paroxysmal dyskinesia is a group of disorders that includes paroxysmal kinesigenic dyskinesia, episodic ataxia, paroxysmal hypnogenic dyskinesia, paroxysmal exertion-induced dyskinesia, and paroxysmal non-kinesigenic dyskinesia. The paroxysmal dyskinesias are a hyperkinetic disorder characterized by intermittent involuntary movements consisting of symptoms from other movement disorders such as chorea, athetosis, dystonia, and ballismus. Episodes of paroxysmal dyskinesias can last from a few seconds to several days. Episodic ataxias are characterized by intermittent episodes of ataxia that can last seconds to hours. Paroxysmal dyskinesias may be triggered by prolonged exertion, sleep, stress, alcohol, coffee, tea, fatigue, sudden voluntary movement, heat, or cold.

Athetosis is a disorder characterized by movements that are continuous, slow, and writhing. The movements are commonly appendicular and frequently involve muscles in the face, neck, and tongue. The condition may occur at rest or when executing voluntary movement. The speed of movements in affected persons can sometimes increase and symptoms are similar to those of chorea (called choreoathetosis). Athetosis movements can blend with those of dystonia, if the muscular contractions are sustained and cause abnormal posturing.

Ballismus are large choreic movements that are fast and usually affect the limbs. Affected individuals exhibit flinging and flailing movements. Commonly, ballismus affects one side of the body (unilateral), producing a condition called hemiballismus.

Akathisia refers to complex movements such as tics, compulsions, and mannerisms that are stereotypic and usually relieved when executing a motor act. Typically, when sitting, the akathitic persons may exhibit movements that include symptoms such as crossing and uncrossing the legs, squirming, pacing, stroking the scalp, or rocking the body. Patients may have burning sensations on the specific affected body part, and they may vocalize a continual moaning and groaning.

Tics can be divided into two disorders: motor tics (abnormal movements) and/or vocal tics (abnormal sounds). Children can present with a chronic disorder of both motor and vocal tics (Gilles de la Tourette syndrome). Movements of simple tics may be very similar to a choreic or myoclonic jerk (abrupt, single, sudden, isolated). Complex tics are movements that are distinctly coordinated patterns of sequential movements, but they may not be identical from occurrence to occurrence and they can occur in different body areas. Tics are rapid movements and, if contractions are sustained in affected body parts, they resemble dystonic movements. One of the major clinical signs that help distinguish tics from other dyskinesias is the presence of involuntary ocular (eye) movement in persons affected with tics. The ocular manifestations of tics can include a brief jerk of the eyes or a sustained eye deviation. Two other dyskinesias, myoclonus and dystonia, can present with involuntary ocular manifestations. With vocal tics, affected persons can exhibit grunts, throat-clearing sounds, or even the utterance of obscenities (coprolalia). Phonic tics (involving nasal and vocal muscles) can be divided into simple phonic tics such as throat-clearing or sniffing or complex phonic tics that include bark-like noises and verbalizations.

Sterotypies are movements that are frequent and may last for minutes. These movements are repetitive and identical (continuous stereotypy.) The bizarre movements associated with mental retardation, autism, and schizophrenia are stereotypies. Continuous stereotypy is characteristic of another type of dyskinesia called tardive dyskinesia, which results from treatment with neuroleptic and antipsychotic medications.

Tardive (late-onset) dyskinesia refers to a group of movement disorders that are characterized by hyperkinetic involuntary movements, consisting of mixed manifestations of orofacial dyskinesia, chorea, tics, and/or athetosis. Abnormal movement can affect muscles in the lips, face, trunk, tongue, and extremities, which can interfere with eating and dexterity. The most characteristic symptom of tardive dyskinesia is orofacial dyskinesia, which usually starts with slow, mild tongue movements followed by exaggerated movements of lips and tongue. Affected individuals can have symptoms that may progress to chewing movements, blinking, bulging cheeks, grimacing, arching eyebrows, and blepharospasms. Tardive dyskinesias are commonly seen in patients taking certain medications such as neuroleptics and antipsychotic medication that are prescribed for schizophrenia, schizoaffective disorder, or bipolar disorder. Other types of tardive dyskinesias include tardive akathisia, tardive dystonia, tardive myoclonus, tardive Tourettism, tardive tremor, and blepharospasm. Approximately 50% of patients taking dopamine receptor blocker medication will develop a form of tardive dyskinesia. Tardive akathisia refers tapping, squirming, and marching movements that are repetitive. Movements associated with tardive dystonia can include a fixed posturing of face and neck, trunk, and extremities. Persons affected with tardive myoclonus, which is a rare disorder, exhibit brief jerky movements of muscles in the face, neck, trunk, arms, and legs. Symptoms of tardive Tourettism usually begins in persons older than 21 years of age and include frequent, multiple tics that are both vocal and motor. This disorder should not be confused with Tourette syndrome, which commonly presents by seven years of age. Tardive tremors often present as involuntary rhythmical, wave-like, and persistent movements of the head, neck, limbs, or voice. Tardive tremors are present both at rest and during voluntary movement.

Early myoclonic encephalopathy is a rare disorder, in which the incidence is approximately one in 40,000 children. It is characterized by brief and abrupt myoclonic jerks (common occurrence in 90% of patients) and seizures. The onset of symptoms usually occurs within the first three years of life. Treatment and management depends on the underlying cause of seizures. Typically, patients receive antiepileptic medications, and improvement of symptoms is usually associated with a good prognosis. If symptoms do not improve with antiepileptic medication(s), the prognosis is not favorable.

Dementia

"Dementia" refers to the loss of significant cognitive function to the degree that behavior and quality of life are materially affected. Dementia typically manifests itself in memory loss, diminished mathematical and analytical abilities, and impaired organizational and executive functioning.

Based on autopsy results, dementia has been estimated to occur in twenty to thirty percent of the world's population. Incidence in the United States is expected to increase markedly as our population ages. Dementia is often progressive, and dementia patients suffer materially higher incidence of trauma, abuse, suicide and other serious illnesses. Dementia results in emotional suffering and financial hardship, both for the patient and his or her family.

The most common causes of dementia are vascular impairments such as strokes (30 to 40 percent), neuro-degenerative disorders such as Alzheimer's Disease, multiple sclerosis and Parkinson's Disease (25 to 40 percent), medical disorders such as EtOH, hepatic failure and hypoglycemia (20 percent), and space-occupying lesions such as brain tumors and subdural hematomas.

Effective treatments for neuro-degenerative dementia are essentially non-existent. Although some medications have been marketed for the treatment of Alzheimer's Disease, such as COGNEX® (tacrine) and ARICEPT® (donepezil), their effectiveness has proven to be minimal and non-sustained.

Symptoms of dementia vary considerably by the individual and the underlying cause of the dementia. Most people affected by dementia have some (but not all) of these symptoms. The symptoms may be very obvious, or they may be very subtle and go unrecognized for some time. The first sign of dementia is usually loss of short-term memory. The person repeats what he just said or forgets where she put an object just a few minutes ago.

Other symptoms and signs for early dementia are as follows: word-finding difficulty—May be able to compensate by using synonyms or defining the word, forgetting names, appointments, or whether or not the person has done something; losing things, difficulty performing familiar tasks—Driving, cooking a meal, household chores, managing personal finances, personality changes (for example, sociable person becomes withdrawn or a quiet person is coarse and silly), uncharacteristic behavior, mood swings, often with brief periods of anger or rage, poor judgment, behavior disorders—paranoia and suspiciousness, decline in level of functioning but able to follow established routines at home, confusion, and disorientation in unfamiliar surroundings—May wander, trying to return to familiar surroundings.

Other symptoms and signs for intermediate dementia are as follows: worsening of symptoms seen in early dementia, with less ability to compensate, unable to carry out activities of daily living (eg, bathing, dressing, grooming, feeding, using the toilet) without help, disrupted sleep (often napping in the daytime, up at night), unable to learn new information, increasing disorientation and confusion even in familiar surroundings, greater risk of falls and accidents due to poor judgment and confusion, behavior disorders—Paranoid delusions, aggressiveness, agitation, inappropriate sexual behavior, hallucinations, confabulation (believing the person has done or experienced things that never happened), inattention, poor concentration, loss of interest in the outside world, and abnormal moods (anxiety, depression).

Other symptoms and signs for severe dementia are as follows: worsening of symptoms seen in early and intermediate dementia, complete dependence on others for activities of daily living, may be unable to walk or move from place to place unassisted, impairment of other movements such as swallowing—increases risk of malnutrition, choking, and aspiration (inhaling foods and beverages, saliva, or mucus into lungs), complete loss of short- and long-term memory—may be unable to recognize even close relatives and friends, complications—dehydration, malnutrition, problems with bladder control, infections, aspiration, seizures, pressure sores, and injuries from accidents or falls The person may not be aware of these problems, especially the behavior problems. This is especially true in the later stages of dementia.

Depression in elderly people can cause dementialike symptoms. As many as 40% of people with dementia are also depressed. Common symptoms of depression include depressed mood, loss of interest in activities once enjoyed, withdrawal from others, sleep disturbances, weight gain or loss, suicidal thoughts, feelings of worthlessness, and loss of ability to think clearly or concentrate.

People with irreversible or untreated dementia present a slow, gradual decline in mental functions and movements over several years. Total dependence and death, often from infection, are the last stages.

Dementia is most common in elderly people; it used to be called senility and was considered a normal part of aging. Dementia is not a normal part of aging but is caused by a number of underlying medical conditions that can occur in both elderly and younger persons. In some cases, dementia can be reversed with proper medical treatment. In others, it is permanent and usually gets worse over time.

About 4-5 million people in the United States have some degree of dementia, and that number will increase over the next few decades with the aging of the population. Dementia affects about 1% of people aged 60-64 years and as many as 30-50% of people older than 85 years.

It is the leading reason for placing elderly people in institutions such as nursing homes. Dementia is a very serious condition that results in significant financial and human costs. Many people with dementia eventually become totally dependent on others for their care. Although people with dementia typically remain fully conscious, the loss of short- and long-term memory are universal.

People with dementia also experience declines in any or all areas of intellectual functioning, for example, use of language and numbers; awareness of what is going on around him or her; judgment; and the ability to reason, solve problems, and think abstractly. These losses not only impair a person's ability to function independently, but also have a negative impact on quality of life and relationships.

As noted above, the invention is a combination of a chemical to increase c-GMP levels in the targeted neural synapse and network with a second chemical to increase the levels of the traditional neurotransmitter(s) in the same location. By mass action or kinetic effect, the result is to overcome the dulled and/or failing effective neurotransmission and subsequent cascade regardless of the original location or cause of the neurodegenerative process. In this manner, the failing neurotransmission and secondary cascades will essentially be overridden to function at a higher and more normal level of responsiveness. This reactivation of the failing neurotransmission system may, in fact, effect changes in neuron plasticity, regeneration and apoptosis.

For example, neurodegenerative dementia (of which Alzheimer's Disease and FTDP-12 are examples) can be remediated with a combination of a PI-5 and a CI, since these chemicals target the cortex and neo-cortex, in which these diseases are thought to originate.

Similarly, dyskinesias (of which Parkinson's Disease, restless leg syndrome and progressive supra-bulbar palsy are examples) can be remediated with a combination of a PI-5 and a DI, since these chemicals target the basal ganglia, substantia negra and nigro-striatal pathways, in which these diseases are thought to originate.

Neurodegenerative-related fatigue and bradydinesis/anergy/anhedonia (of which Parkinson's Disease and diffuse neural fibrosis are examples) can be remediated with a combination of a PI-5, an SSRI and an NI, since these chemicals target the brain stem, reticular formation and locus cerruleus, in which these diseases are thought to originate.

Central sleep apneas (of which narcolepsy is an example) can be remediated with a combination of a PI-5, an SSRI and an NI, since these chemicals target the brain stem, reticular formation, Nucleus of Raphe, locus cerruleus and ascending pathways from the reticular-formation to the nigro striatum and substantia negra, in which these diseases are thought to originate.

Amyotrophic lateral sclerosis and diseases of cranial nerves and bulbar dysfunction can be remediated with a combination of a PI-5, an SSRI and an NI, since these chemicals target the brain stem, Nucleus of Raphe, locus cerruleus and cranial nerve nuclei, in which these diseases are thought to originate.

In addition, the treatment of neuro-degenerative dementia (NDD) can be remediated with a combination of a SSRI, a CI and a PI-5. For example, the optimal dosage range may be as follows:

PI-5 (example, CIALIS® (tadalafil))=20 mg to 100 mg/day

SSRI (example, LUVOX® (fluvoxamine))=25 mg to 400 mg/day

CI (example, COGNEX® (tacrine))=10 mg to 160 mg/day

Doses should begin at low levels and be titrated up individually every three days at follow-up visits with the treating physician.

Finally, other neurodegenerative diseases, to be described in the present and in the future as further clinical and laboratory data become available, can be remediated by combining a PI-5 with medication(s) to increase the relevant traditional neurotransmitter(s) that are localized to target the affected areas neuroanatomically and functionally.

The Facilitation and Acceleration of Wound, Burn and Scar Healing and for the Maintenance and Improvement of Skin and Mucous Membrane Health.

Moreover, the compositions of the present invention may be administered to a patient to facilitate or accelerate wound, burn or scar healing or for the maintenance and improvement of skin or mucous membrane health. For instance, the invention provides for treating various diseases (atopy, psoriasis, contact dermatitis, acne, cancer, vasculitis) or traumatic processes (surgery, laceration, burns, infections) which adversely impact the body's appearance. The subject invention involves treating a subject with a PI-5 in combination with one or more SSRIs or CIs. A few exemplary conditions are described in more detail below.

Atopys:

Atopys or atopic dermatitis is a very common, often chronic (long-lasting) skin disease that affects a large percentage of the world's population. It is also called eczema, dermatitis, or atopy. Most commonly, it may be thought of as a type of skin allergy or sensitivity. The atopic dermatitis triad includes asthma, allergies (hay fever), and eczema. There is a known hereditary component of the disease, and it is seen more in some families. The hallmarks of the disease include skin rashes and itching.

The word "dermatitis" means inflammation of the skin. "Atopic" refers to diseases that are hereditary, tend to run in families, and often occur together. In atopic dermatitis, the skin becomes extremely itchy and inflamed, causing redness, swelling, cracking, weeping, crusting, and scaling. Dry skin is a very common complaint and an underlying cause of some of the typical rash symptoms.

Although atopic dermatitis can occur in any age, most often it affects infants and young children. In some instances, it may persist into adulthood or actually first show up later in life. A large number of patients tend to have a long-term course with various ups and downs. In most cases, there are periods of time when the disease is worse, called exacerbations or flares, which are followed by periods when the skin improves or clears up entirely, called remissions. Many children with atopic dermatitis enter into a permanent remission of the disease when they get older, although their skin may remain somewhat dry and easily irritated.

Multiple factors can trigger or worsen atopic dermatitis, including dry skin, seasonal allergies, exposure to harsh soaps and detergents, new skin products or creams, and cold weather. Environmental factors can activate symptoms of atopic dermatitis at any time in the lives of individuals who have inherited the atopic disease trait.

Psoriasis:

Psoriasis affects approximately 2-3% of the world's population and about 7 million people in the U.S. Psoriasis is a chronic, inflammatory, hyperproliferative disease of the skin characterized by well-demarcated, erythematous, scaly plaques. Psoriasis may consist of one or two lesions or may be a widespread dermatosis with disabling arthritis or exfoliation. Although the exact pathogenesis of psoriasis remains undefined, there are several therapeutic options. For example, monoclonal antibodies have been employed in attempts to combat psoriasis, however this treatment option is used primarily to treat generalized psoriasis as opposed to localized psoriasis. Since most sufferers of psoriasis have only localized psoriasis, the mainstay of treatment remains the use of topical agents.

Topical steroids, such as triamcinolone, have been used in the treatment of psoriasis for years. While topical steroids are often effective in the treatment of psoriasis, their use may be associated with adverse side effects such as those described above as well as skin atrophy or systemic effects such as HPA-axis suppression if used extensively.

Contact Dermatitis:

Contact dermatitis is a localized rash or irritation of the skin caused by contact with a foreign substance. Substances that cause contact dermatitis in many people include "poisonous" plants such as poison ivy, certain foods, some metals, cleaning solutions, detergents, cosmetics, perfumes, industrial chemicals, and latex rubber.

There are 2 types of contact dermatitis: allergic and irritant. Allergic contact dermatitis results from a reaction of the immune system. As such, in allergic contact dermatitis, there is a skin reaction to something that has touched the skin at that site. Unlike most allergic reactions, the trigger is external rather than internal. In contrast, irritant contact dermatitis results from coming into contact with a substance that directly damages your skin. Many chemicals, including industrial cleaning products, solvents, detergents can cause this condition.

Acne:

Acne happens when oil (sebaceous) glands come to life around puberty stimulated by male hormones from the adrenal glands of both boys and girls. Oil is a natural substance which lubricates and protects the skin, and under certain circumstances, cells that are close to the surface block the openings of sebaceous glands and cause a buildup of oil underneath. This oil stimulates bacteria, (which live in everyone's skin and generally cause no problems), to multiply and cause surrounding tissues to become inflamed.

If the inflammation is right near the surface, you get a pustule; if it's deeper, a papule (pimple); deeper still and it's a cyst. If the oil breaks though to the surface, the result is a "whitehead." If the oil becomes oxidized (that is, acted on by oxygen in the air), the oil changes from white to black, and the result is a "blackhead."

Skin Cancer.

Skin cancer is the most common of all human cancers. Some form of skin cancer is diagnosed in more than 1 million people in the United States each year.

Cancer occurs when normal cells undergo a transformation during which they grow and multiply without normal controls. As the cells multiply, they form a mass called a tumor. Tumors of the skin are often referred to as lesions.

Tumors are cancerous only if they are malignant such that they encroach on and invade neighboring tissues because of their uncontrolled growth. Tumors may also travel to remote organs via the bloodstream or lymphatic system. Tumors overwhelm surrounding tissues by invading their space and taking the oxygen and nutrients they need to survive and function.

Skin cancers are of three major types: basal cell carcinoma (BCC), squamous cell carcinoma (SCC), and melanoma.

The vast majority of skin cancers are BCCs or SCCs. While malignant, these are unlikely to spread to other parts of the body. They may be locally disfiguring if not treated early. A small but significant number of skin cancers are malignant melanomas. Malignant melanoma is a highly aggressive cancer that tends to spread to other parts of the body. These cancers may be fatal if not treated early.

Like many cancers, skin cancers start as precancerous lesions. These precancerous lesions are changes in skin that are not cancer but could become cancer over time.

Vasculitis:

Vasculitis is a general term for a group of uncommon diseases that feature inflammation of the blood vessels. The blood vessels of the body are referred to as the vascular system. The blood vessels are comprised of arteries that pass oxygen-rich blood to the tissues of the body and veins that return oxygen-depleted blood from the tissues to the lungs for oxygen. Vasculitis is characterized by inflammation in and damage to the walls of various blood vessels.

Each of the vasculitis diseases is defined by certain patterns of distribution of blood vessel involvement, particular organ involvement, and laboratory test abnormalities. As a group, these diseases are referred to as vasculitides.

The actual cause of these vasculitis diseases is usually not known. However, immune system abnormality and inflammation of blood vessels are common features. Each form of vasculitis has its own characteristic pattern of symptoms, much of which depends on what particular organs are affected.

Examples of vasculitis include Kawasaki disease, Behcet's disease, polyarteritis nodosa, Wegener's granulomatosis, cryoglobulinemia, Takayasu's arteritis, Churg-Strauss syndrome, giant cell arteritis (temporal arteritis), and Henoch-Schönlein purpura.

Traumatic Processes (Surgery, Laceration, Burns, Infections)

Scar formation is a natural part of the healing process after injury. Various factors influence how skin scars such as the depth and size of the wound or incision and the location of the injury. In addition, age, heredity, sex and ethnicity influence how a person's skin will react to a wound and scar.

These are several different types of scars. Keloid scars are the result of an overly aggressive healing process. These scars extend beyond the original injury. Over time, a keloid scar may affect mobility. Possible treatments include surgical removal, or injections with steroids. Smaller keloids can be treated using cryotherapy (freezing therapy using liquid nitrogen). Keloid formation may be prevented by using pressure treatment or gel pads with silicone once an injury is sustained.

Contracture scars result from skin burns in which skin tightens and impairs the ability to move. In certain cases, this type of scar may go deeper to affect muscles and nerves.

Hypertrophic scars are raised and red scars that are similar to keloids but do not breach the boundaries of the injury site.

Therapeutic levels of the three combined drugs will vary from individual to individual and from disorder to disorder. The combination of SSRI, CI and PI medications in the appropriate amounts and intervals effective to treat any particular burn, scar, wound, disease or disorder of the mucocutaneous system will necessarily be monitored both clinically and chemically by the family practitioner, dermatologist, internist or neurologist. This formulation can eventually take the form of a combined pill given daily, a daily or weekly patch, a long-term injection, or an implant.

An exemplary optimal dosage range is as follows:

PI-5(example, CIALIS® (tadalafil))=5 mg to 80 mg/day

SSRI (example, LUVOX® (fluvoxamine))=12.5 mg to 400 mg/day

CI (example, COGNEX® (tacrine))=5 mg to 60 mg/day

In general, the optimal dosage intervals (oral preparation) will be as follows:

SSRI=1× to 4×/day
PI=1× to 4×/day
CI=1× to 4×/day

Doses should begin at low levels and be titrated up individually every three days at follow-up visits with the treating physician To ensure maximum patient safety, monitoring should include blood tests for liver and kidney function, as well as electrolyte levels as is the current standard of care when administering the individual drugs. In addition, thorough physical exams, including EKG and probably treadmill tests, should be performed prior to starting treatment. FIG. 1 provides a flowchart of the proposed methodology. Doses may need to be decreased with prolonged use, due to the potential for remission or even cure due to selective neuroregeneration, reproduction and plasticity.

In each of the foregoing examples, the PI-5 acts to increase nitric oxide levels in the targeted synapses and to increase the secondary messenger, c-GMP. The resulting increased c-GMP acts in concert with the relevant traditional neurotransmitter upon the efferent neuron receptor protein and other structures to correctly modulate the receptor's activity. This correct modulation ameliorates defective neuron synapse activation and may also effect neuron regeneration and plasticity.

Although the above discussion has focused on a small handful of potential mechanisms of action for the inventive combination, the invention itself is directed to a pharmaceutical composition and treatment regime consisting of the administration of two or more medications, one to increase the synaptic concentration of c-GMP and the other(s) to increase the synaptic concentration(s) of the traditional neurotransmitter(s) known to operate in the targeted area(s) of the human brain.

To ensure maximum patient safety, monitoring should include blood tests for liver and kidney function, as well as electrolyte levels as is the current standard of care when administering the individual drugs. In addition, thorough physical exams, including EKG and probable treadmill tests, should be performed prior to starting treatment. Doses may need to be revised with prolonged use due to the potential for remission or even cure due to selective neuroregeneration, reproduction and plasticity or due to exacerbation of disease. FIG. 1 provides a flowchart of the proposed methodology. Doses may need to be decreased with prolonged use, due to the potential for remission or even cure due to selective neuroregeneration, reproduction and plasticity.

Regardless of the actual dosage regime chosen, the therapeutically effective level should be that which does not cause significant side effects, but minimizes symptoms of the neurological disorder. In the context of the current treatment regime, this level should not be the dosage level at which improvement begins, but that at which improvement peaks and is maximized. This dosage may change over time, but should mainly reflect changes in the patient's physical state including, for example, volume of distribution, renal and liver function, weight, and change in underlying disease.

Kits:

Also provided are kits for practicing the subject methods. The subject kits may vary greatly in regards to the components included. The subject kits at least include a PI-5 in combination with one or more SSRIs, SNRIs, CIs, DIs, or OIs in separate and discrete dosage forms, and instructions for its use.

In certain embodiments, the subject kits include instructions for a patient to carry out drug administration to treat a neurodegenerative disease or to facilitate or accelerate wound, burn and scar healing and maintain and improve skin and mucous membrane health. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit. In certain aspects, the subject kit comprises a sealed package of controlled release dosage forms wherein the dosage forms provide a PI-5 in combination with one or more SSRIs, SNRIs, CIs, DIs, or OIs in separate and discrete dosage forms, and instructions for its use.

This invention is further illustrated by the following examples which should not be construed as limiting. The contents of all references, patents and published patent applications cited throughout this application are hereby incorporated by reference.

EXAMPLE 1

A 58-year old Caucasian male patient with moderate NDD secondary to Parkinson's Disease was administered a combination of PI-5, SSRI, and CI. Patient has been suffering from Parkinson's for an approximate 12-year duration with no other significant co-morbidities. Patient weighed 210 lbs with a body mass index (bmi) of 0.20. Patient has had a recent, seven-month progression of somatic symptoms with moderate progression of apraxia, bradykinesia and loss of short-term and intermediate visual and verbal memory, combined with decreased analytic ability, mathematic ability, creativity and organizational skills. Initial tests were run for kidney function and liver function. The kidney function tests showed a creatinine level of 1.0, and a liver function test (LFT), both of which were within normal limits. Workup as standard for dementia, including CBC, SMAC, UA, EKG, CXR, MRI brain (no gadolinium), syphilis titres, AIDS test, pulse oximitry, sedimentation rate, thyroid function tests and B-12 level An initial trial of L-dopa (SINEMET® (carbidopa-levodopa)) only resulted in transient success and mild changes in rigidity and tremor, followed by mild worsening. Another trial of COGNEX® (tacrine) and aspirin resulted in no changes in dementia. After four weeks of the regimen of LUVOX® (fluvoxamine) and CIALIS® (tadalafil) set forth in Table 1, below, a 20 percent improvement in rated dementia was observed. After one additional week of the regimen of LUVOX® (fluvoxamine), CIALIS® (tadalafil) and COGNEX® (tacrine) set forth in Table 1, below, a 95 percent improvement in rated dementia was observed. This level of improvement has been sustained without significant 'on/off' for ten months without significant side effects, either clinically or chemically.

TABLE 1

| Week of Trial | Medication 1 - Luvox | Medication 2 - Cialis | Medication 3 - Cognex |
|---|---|---|---|
| 1 | 12.5 mg BID | 10 mg BID | None |
| 2 | 25 mg BID | 10 mg BID | None |
| 3 | 50 mg BID | 20 mg BID | None |
| 4 | 100 mg TID | 20 mg TID | None |
| 5 | 100 mg TID | 20 mg TID | 10 mg TID |

Although the above provides effective doses with the selected medications, it should be understood that one of ordinary skill in the art should be able to establish comparable doses with other combinations of existing and future SSRI, CI and PI-5 medications using similar titration techniques, depending on choices of half-life and other properties.

EXAMPLE 2

A second subject was diagnosed with nonspecific but rapidly progressive multi-system neurodegenerative disease at age 57. Clinical progression and further diagnostic findings suggest probable frontotemproral dementia with cortico-bulbar disease. Initial presentation was with abrupt onset dementia with rapid progression over 3-4 months. Severe, generalized myoclonus of high amplitude with ataxia, dyspahgia, central and peripheral respiratory distress (requiring CPAP), dizziness, and hypokinetic rigidity followed some one month later and have continued to progress as well as dementia.

Patient also suffered for approximately 10 years from mild facial acne which has been responsive to topical and oral antibiotics, digital vitiligo, and one scar of 4×4 cm atrophic hypopigmentation on left upper thigh secondary to a chemical burn thirty years ago. Mild intermittent gingival infections requiring minimal surgical intervention with retraction from tooth line for over ten years.

Work-up for patient has included the following findings:
1/MRI brain×2 (onset/20 months later) without contrast-wnl
2/SPECT (20 months into disease course) on medications-wnl
3/Sleep study (24 months into disease course) off medication—markedly abnormal with frequent central and peripheral hypopnic episodes, Oxygen saturations deteriorating to 80-90%.
4/Positive allele 4,5 for Apolipoprotein e
5/Positive serum assay for KCNC3 variants (major dominant locus determinant for ataxia)
6/elevated homocysteine-25

Patient was a non-smoker with no alcohol or other drug consumption. Patient suffered from coexisting prior problem of chronic atrial fibrillation, currently rate controlled with exercise alone and anticoagulation intermittently with Coumadin.

Positive family history for father who died at age 62 of complications resulting from a fall in a custodial nursing home. No family history of cancer of major skin disorders. Father and mother both required multiple dental extractions and subsequent dentures secondary to both gingival infections and carries. Diagnosis at time in father of end stage Parkinson's Disease. Poor response to multiple regimens of dopamine agonists, cryosurgical ablation of lateral basal ganglia.

Patient was initially treated individually with SINEMET® (carbidopa-levodopa), COGNEX® (tacrine) (cholinesterase inhibitor,) LUVOX® (fluvoxamine) (SSRI), CIALIS® (tadalafil) and VIAGRA® (sildenafil) (phosphodiesterase 5 inhibitors) without any clinical response to neurological disease, skin and mucous membrane disorders. However, either phosphodiesterase 5 inhibitor in combination with either or both COGNEX® (tacrine) or LUVOX® (fluvoxamine) produced a dramatic improvement in all neurological symptoms and in skin disorders. Mucous membrane decline in separation from native teeth also improved. The patient's scar was not effected.

Patient had greatest improvement noted in mucocutaneous systems and neurologically with combination of Phosphodiesterase 5 inhibitor, SSRI, and cholinesterase inhibitor taken orally. A 90% improvement in mucocutaneous diseases noted and maintained during course of treatment. Effects of medications in all parameters noted within: 20 minutes, maximum response seen within three doses of each medicine. Optimal combination, with essentially no side effects, noted and maintained for 20 months on CIALIS® (tadalafil)—5 mg oral TID, COGNEX® (tacrine)—10 mg oral TID, LUVOX® (fluvoxamine)—100 mg oral TID. The twenty four hour doses, put into 7.5 cc of water solution, was also applied topically to scar noted previously. Ten percent scar retraction was noted in one week, and 95% resolution of scar and replacement by visually normal tissue occurred at 2 months. Ekg, CBC, UA, LFT, renal function, Calcium, TFT have remained normal at onset of disease and at 4 month follow-up on oral medications. Rare dry mouth noted with normal glucose. Occasional frontal headache relieved quickly with low dose oral TYLENOL® (acetaminophen). VIAGRA® (sildenafil) is equivalently substituted for oral CIALIS® (tadalafil) at a dose of 50 mg TID. Paxil is equivalently substituted for LUVOX® (fluvoxamine) at a dose of 20 mg TID. Patient also takes Folic acid—1 mg per day, and Vitamin B6. Repeated attempts to wean off chronic medications has resulted in return of neurological, mucocutaneous abnormalities within 5 days.

EXAMPLE 3

A third subject was diagnosed with atypical Parkinson's Disease with an initial presentation fifteen years earlier with cogwheel type diffuse tremor of low amplitude, diffuse muscular rigidity, mild bradykinesia, gait abnormalities. Patient also suffered from severe seborrheic dermatitis and scarring facial acne rosacea for over 25 years and noted only a minimal response to topical and oral antibiotics. All symptoms slowly progressed to the present state of advanced severity in all symptoms and signs. Significant work-up has included the following:
  1/MRI brain (without contrast)×⅔ years post onset, 15 years later)-wnl
  2/PET brain (unclear isotopes/10 years into disease)—symmetrical abnormalities in cortex (further details unavailable at this time).
  3/paradoxical response to IV Apomorphine with decreased blood pressure and worsening of rigidity and tremor.

Patient is a non-smoker and social drinker with minimal alcohol consumption and no history of drug abuse. Chronic problems of borderline hypertension (treated with diet and HYTRIN® (terazoin)), benign prostatic hypertrophy (treated with HYTRIN® (terazoin) and voding training), GERD treated intermittently as needed with PRILOSEC® (omeprazole) plus PEPCID® (famotidine) for short periods, DJD of cervical and lumbar spine treated intermittently with physical therapy, TYLENOL® (acetaminophen), occasional VICODIN® (acetaminophen/hydrocodone) as needed.

Patient was treated chronically with low-dose Amantadine with little or no improvement of all symptoms. No change in seborrheic dermatitis or acne rosacea.

When initially treated with SINEMET® (carbidopa-levodopa) and MIRAPEX® (pramipexole) on two separate occasions, patient had a mild worsening of all neurological symptoms. Nine months ago patient started treatment on CIALIS® (tadalafil) (phosphodiesterase 5 inhibitor) in combination with LUVOX® (fluvoxamine) (S SRI) and COGNEX® (tacrine) (cholinesterase inhibitor) in combination with Amantadine. Improvement noted subjectively by patient in neurological symptoms at 20 minutes with maximum improvement after three doses. No improvement occurred with any of the drugs individually or with any combination of above drugs without the phosphodiesterase 5 inhibitor.

Mild improvement in seborrheic dermatitis noted at 3 days and mild improvement in acne rosacea noted at 10 days. Maximal improvement in all neurological and mucocutaneous problems on the following continuing doses: COGNEX® (tacrine)—10 mg oral TID/LUVOX® (fluvoxamine)—100 mg oral TID/CIALIS® (tadalafil)—30 mg oral TID/others as prior to treatment.

Patient has maintained 80% improvement in all symptoms during 9 month treatment. Seborrheic dermatitis has 95% resolved, acne rosacea has 80% resolved without antibiotic treatment. Baseline and every 4 month ekg, CBC, LFT, Calcium, BUN, CXR have remained normal. Occasional nausea has occurred but resolved within several hours with short treatment of PRILOSEC® (omeprazole) and PEPCID® (famotidine).

EXAMPLE 4

A fourth subject was diagnosed with Parkinson's Disease and administered a combination of PI-5, SSRI and DI. Initial presentation with asymmetric tremor of right hand and generalized stiffness. Slow progression over 20 years to include severe diffuse cogwheel rigidity, diffuse pill rolling tremor, severe bradykinesia with microphonia, essentially immobile with severe gait abnormalities, mask-like face.

Workup included the following:
  1/CT brain(without contrast/onset of disease)-wnl 4/carotid duplex(4 years earlier)-wnl 2/MRI brain (without contrast/10 years into disease)-wnl 3/TSH minimally elevated at 6.5, but with normal T3/T4 4/cholesterol mildly elevated at 210, LDL 160. Intermittently treated with statin with decreases to 160, 120 respectively.

Patient smokes 15 packs of cigarettes per year but not for 20 years. No alcohol and no illicit drug abuse. Medical problems including asthma, low grade treated only intermittently with inhaled B agonist. Basal cell carcinoma of right dorsum hand, successfully excised locally without recurrence.

Patient continued on chronic Sinamet with initial mild response in rigidity.

Patient then tried for short periods later in disease on MIRAPEX® (pramipexole), Bromocriptine without significant change. Six months ago, patient started treatment on LUVOX® (fluvoxamine), CIALIS® (tadalafil) (phosphodiesterase 5 inhibitor) in addition to SINEMET® (carbidopa-levodopa). Noted initial improvement within 1 hour of taking all medications, maximum improvement at 4 doses. No changes noted with any combination of above drugs unless CIALIS® (tadalafil) included.

Maximal improvement, approximately 80 percent in all symptoms) occurred on following regimen maintained for 6 months. LUVOX® (fluvoxamine)—400 mg po per day in three divided doses/CIALIS® (tadalafil)—20 mg po per day in three divided doses/others as before. Note that COGNEX® (tacrine) (cholinesteras inhibitor) induced mild improvements in all symptoms when added to above regimen, but was discontinued secondary to gastrointestinal upset.

No significant side effects as above, with normal BC, Creatinine/LFT/TSH/ekg/cxr/Calcium at baseline, 1 month into treatment and 5 months into treatment. Noted incidentally is 80% resolution of chronic acne rosacea.

EXAMPLE 5

A fifth subject was diagnosed with Alzheimer's Disease and dementia and administered a combination of PI-5, SSRI and CI. Initial presentation with short-term forgetfulness. Progression over 15 years to severe dementia with loss of short and intermediate memory, executive function, decision making, etc. Patient hospitalized in custodial Alzheimer's nursing home with indwelling Foley catheter secondary to incontinence with intermittent outlet voiding obstruction and intermittent, recurrent lower urinary tract infections requiring chronic suppressive antibiotics. PEG feeding tube placement 4 years ago secondary to malnutrition, dysphagia.

Significant past workup includes:
  1/CT head (without IV contrast/12 years ago)-wnl 2/Carotid duplex (6 years ago)-mild, non-obstructive plaque R internal carotid.

3/Lumbar puncture (4 years ago during febrile confusion)-wnl

Patient did not smoke or abuse illicit drugs. Patient moderately consumed heavy alcohol but not for approximately 34 years (no complications recorded).

Patient placed on initial COGNEX® (tacrine) (cholinesterase inhibitor), then later ARICEPT® (donepezil) without significant clinical status changes. Seven months ago, patient restarted taking COGNEX® (tacrine) in addition to LUVOX® (fluvoxamine) (SSRI) and CIALIS® (tadalafil) (phosphodiesterase 5 inhibitor). No significant change noticed until 2 weeks into maximal therapy. Slow improvement in all symptoms occurred over 6 weeks to approximately 45 percent of baseline. Patient is now taking oral liquids and solids although continuing with tube feeding. In addition, the Foley catheter has been discontinued.

Patient still has moderate dementia but with improved short term recall. Patient speaks in short, monosyllabic sentences and appropriate response to verbal stimulus. Family has removed patient to their home with visiting home nurse and physical therapy services.

No improvement was noted with any single medication or combination of medications not including a phosphodiesterase 5 inhibitor. Maximal improvement has been maintained for 6 months on the following.

COGNEX® (tacrine)—90 mg per day in three divided doses/LUVOX® (fluvoxamine)—400 mg per day in three divided doses/CIALIS® (tadalafil)—20 mg per day in two divided doses).

No significant side effects have occurred, and ekg, CBC, BUN, Cr, TSH, Calcium, LFT have remained within normal limits. For a two week period, ARICEPT® (donepezil) was successfully substituted for COGNEX® (tacrine) without noticeable changes.

Equivalents:

Those skilled in the art will recognize, or be able to ascertain using no more than routine experimentation, numerous equivalents to the specific procedures described herein. Such equivalents are considered to be within the scope of the present invention and are covered by the following claims. Various substitutions, alterations, and modifications may be made to the invention without departing from the spirit and scope of the invention as defined by the claims. Other aspects, advantages, and modifications are within the scope of the invention. The contents of all references, issued patents, and published patent applications cited throughout this application are hereby fully incorporated by reference. The appropriate components, processes, and methods of those patents, applications and other documents may be selected for the present invention and embodiments thereof.

The invention claimed is:

1. A composition comprising fluvoxamine and a phosphodiesterase 5 inhibitor, wherein the phosphodiesterase 5 inhibitor is selected from the group consisting of tadalafil, vardenafil, sildenafil, and zaprinast in combination with at least one of the following medications:
   a cholinesterase inhibitor, wherein the cholinesterase inhibitor is selected from the group consisting of tacrine and donepezil; and
   a dopamine agonist, wherein the dopamine agonist is selected from the group consisting of levodopa, bromocryptine, carbidopa/levodopa, and pramipexole.

2. The composition of claim 1, wherein the phosphodiesterase inhibitor 5 inhibitor is tadalafil.

3. The composition of claim 2, wherein the cholinesterase inhibitor is tacrine.

4. A kit comprising a packaged combination of the composition of claim 1, wherein each medication is formulated in a separate and discrete dosage form.

5. The composition of claim 1, wherein the medications are administered individually.

6. The composition of claim 1, wherein the medications are in a combined form selected from the following:
   a once-weekly patch;
   a monthly patch;
   a long-term injection;
   a combined pill; and
   an implant.

7. The composition of claim 1, comprising 5 mg to 80 mg of tadalafil.

8. The composition of claim 1, comprising 12.5 mg to 400 mg of fluvoxamine.

9. The composition of claim 1, comprising 5 mg to 60 mg of tacrine.

* * * * *